United States Patent
Ambade et al.

(10) Patent No.: US 10,464,929 B2
(45) Date of Patent: Nov. 5, 2019

(54) ORGANIC MOLECULES FOR TERAHERTZ TAGGING APPLICATIONS

(71) Applicant: Council of Scientific & Industrial Research, New Delhi (IN)

(72) Inventors: Ashootosh Vasant Ambade, Maharashtra (IN); Bala Pesala, Chennai (IN); Kavita Joshi, Maharashtra (IN); Nitin Bapurao Basutkar, Maharashtra (IN); Shaumik Ray, Chennai (IN); Jyotirmayee Dash, Chennai (IN); Kaware Vaibhav Vilasrao, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 233 days.

(21) Appl. No.: 15/111,167

(22) PCT Filed: Jan. 13, 2015

(86) PCT No.: PCT/IN2015/050005
§ 371 (c)(1),
(2) Date: Jul. 12, 2016

(87) PCT Pub. No.: WO2015/104722
PCT Pub. Date: Jul. 16, 2015

(65) Prior Publication Data
US 2016/0335827 A1 Nov. 17, 2016

(30) Foreign Application Priority Data
Jan. 13, 2014 (IN) ............. 0095/DEL/2014

(51) Int. Cl.
*G07D 7/1205* (2016.01)
*C07D 409/12* (2006.01)
*C07D 213/74* (2006.01)
*C07D 239/54* (2006.01)

(52) U.S. Cl.
CPC ......... *C07D 409/12* (2013.01); *C07D 213/74* (2013.01); *C07D 239/54* (2013.01); *G07D 7/1205* (2017.05)

(58) Field of Classification Search
CPC .................................................. G07D 7/1205
See application file for complete search history.

(56) References Cited

U.S. PATENT DOCUMENTS

| 3,776,917 A | 12/1973 | Mann et al. |
| 3,979,408 A | 9/1976 | Trani |
| 4,132,713 A | 1/1979 | Broadhurst |
| 2008/0039633 A1 | 2/2008 | Jung et al. |

FOREIGN PATENT DOCUMENTS

| WO | WO 2004/081545 A1 | 9/2004 |
| WO | WO 2010/020407 A2 | 2/2010 |
| WO | WO 2011/004393 A2 | 1/2011 |
| WO | WO 2013/106728 A1 | 7/2013 |

OTHER PUBLICATIONS

King, M.D. et al. 2010 "Discrimination of Chiral Solids: A Terahertz Spectroscopic Investigation of L-and DL-Serine" *J Phys Chem A* 114: 2945-2953.
Zheng, Z.-P. et al. 2012 "Application of terahertz spectroscopy and molecular modeling in isomers investigation: Glucose and fructose" *Optics Communications* 285: 1868-1871.
Chen, et al. 2001 "Supramolecular liquid crystals with hydrogen-bonding self-assembled T-shaped mesogens." *Chemistry Letters* 11: 1156-1157.
Laman, et al. 2008 "High-resolution waveguide THz spectroscopy of biological molecules" *Biophysical Journal* 94(3): 1010-1020.
Langer, et al. 2005 "3, 5, 7, 9-tetraphenylhexaazaacridine: A highly stable, weakly antiaromatic species with 16 π electrons" *Angewandte Chemie* 44(33): 5255-5259.
Manesiotis, et al. 2005 "Improved imide receptors by imprinting using pyrimidine-based fluorescent reporter monomers" *The Journal of Organic Chemistry* 70(7): 2729-2738.
Osmialowski, et al. 2010 "Complexation of 2,6-bis(acylamino) pyridines with dipyridin-2-ylamine and 4, 4-dimethylpiperidine-2, 6-dione" *The Journal of Physical Chemistry A* 114(49): 12881-12887.
Yang, et al. 2013 "Copper-catalyzed dehydrogenative reaction: synthesis of amide from aldehydes and aminopyridine" *Tetrahedron* 69(31): 6431-6435.

*Primary Examiner* — Joseph R Kosack
(74) *Attorney, Agent, or Firm* — Knobbe, Martens, Olson & Bear LLP

(57) ABSTRACT

Substituted heterocyclic compounds and/or aromatic compounds containing amide and/or urea groups exhibit resonance in the range of 0.1-10 THz. Binary molecular complexes can be based on the substituted heterocyclic compounds and/or aromatic compounds containing amide and/or urea groups. The compounds and binary molecular complexes have varying molecular mass and hydrogen bond strengths demonstrating several resonances below 10 THz. The compounds and binary molecular complexes are customizable for various applications, such as authentication of a product.

5 Claims, 11 Drawing Sheets

THz spectra of Ph-DAP (2-10 THz)
THz spectra of Ph-DAP (below 1 THz)
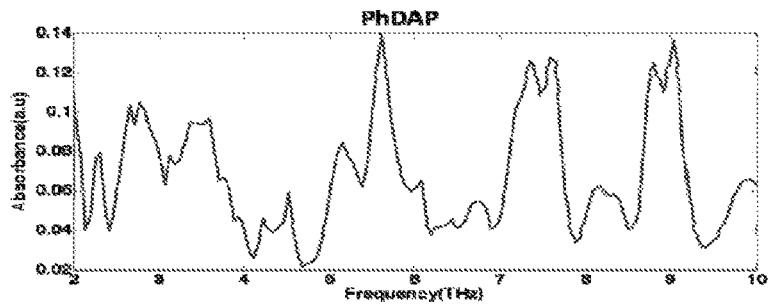
Fig: 1
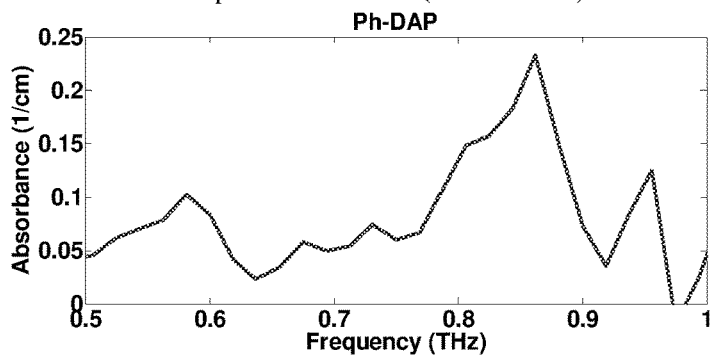
Fig: 2
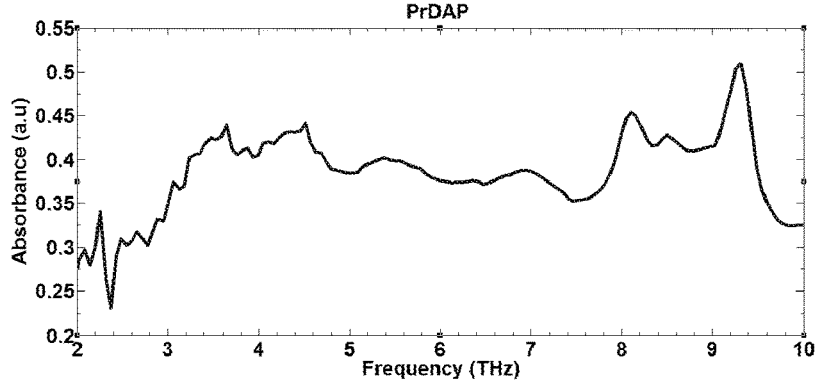
Fig: 3

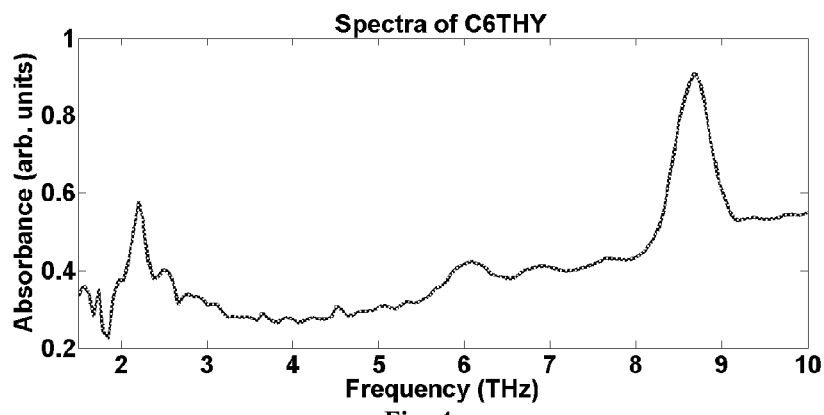
Fig: 4
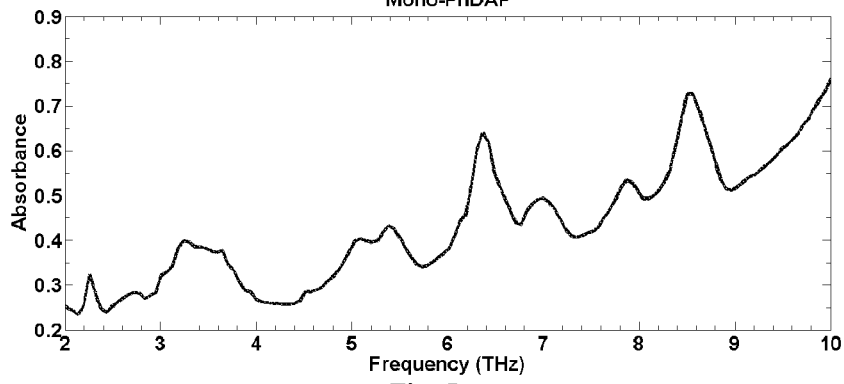
Fig: 5
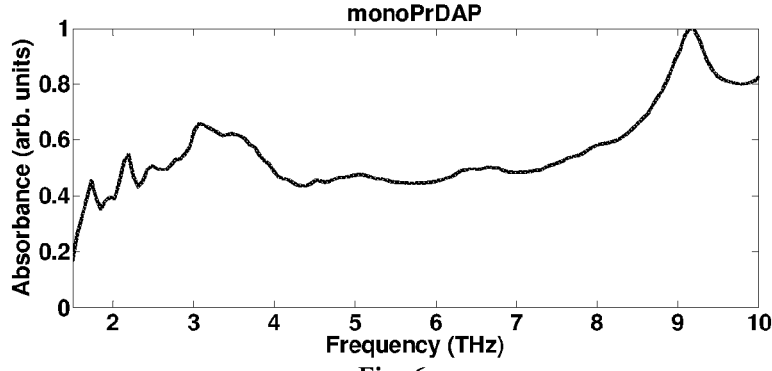
Fig: 6
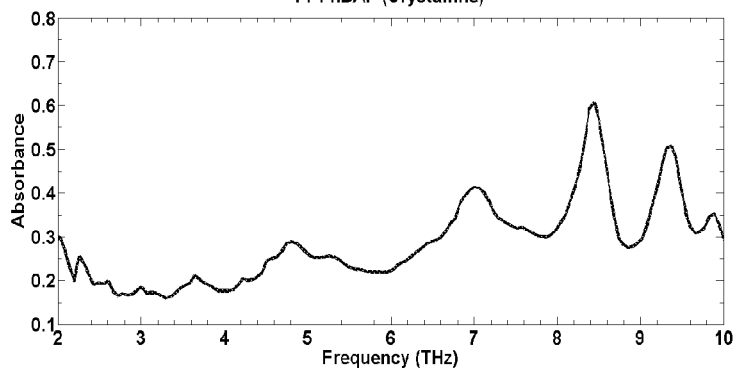
Fig: 7

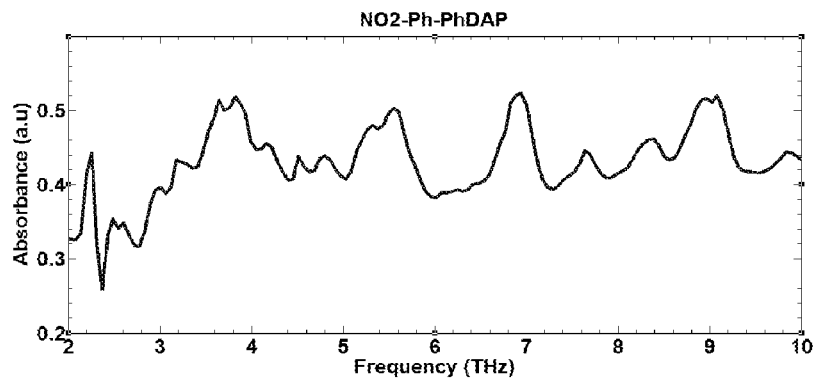
Fig: 8
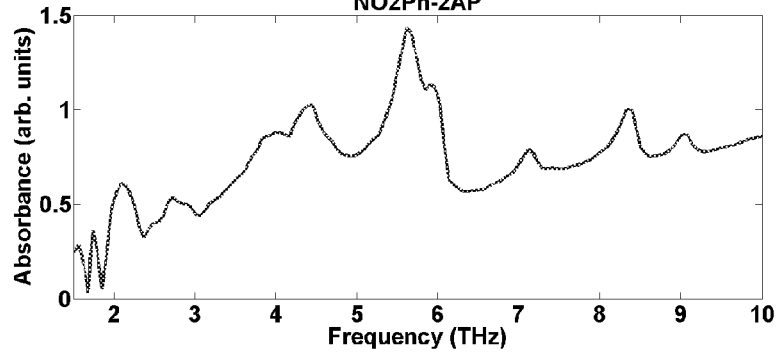
Fig: 9
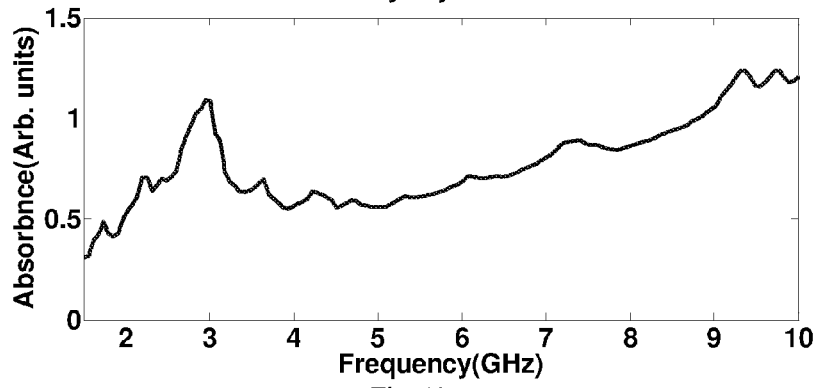
Fig: 10
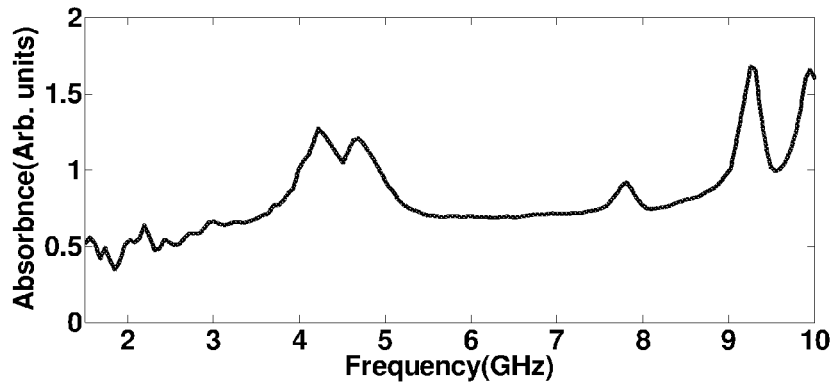
Fig: 11

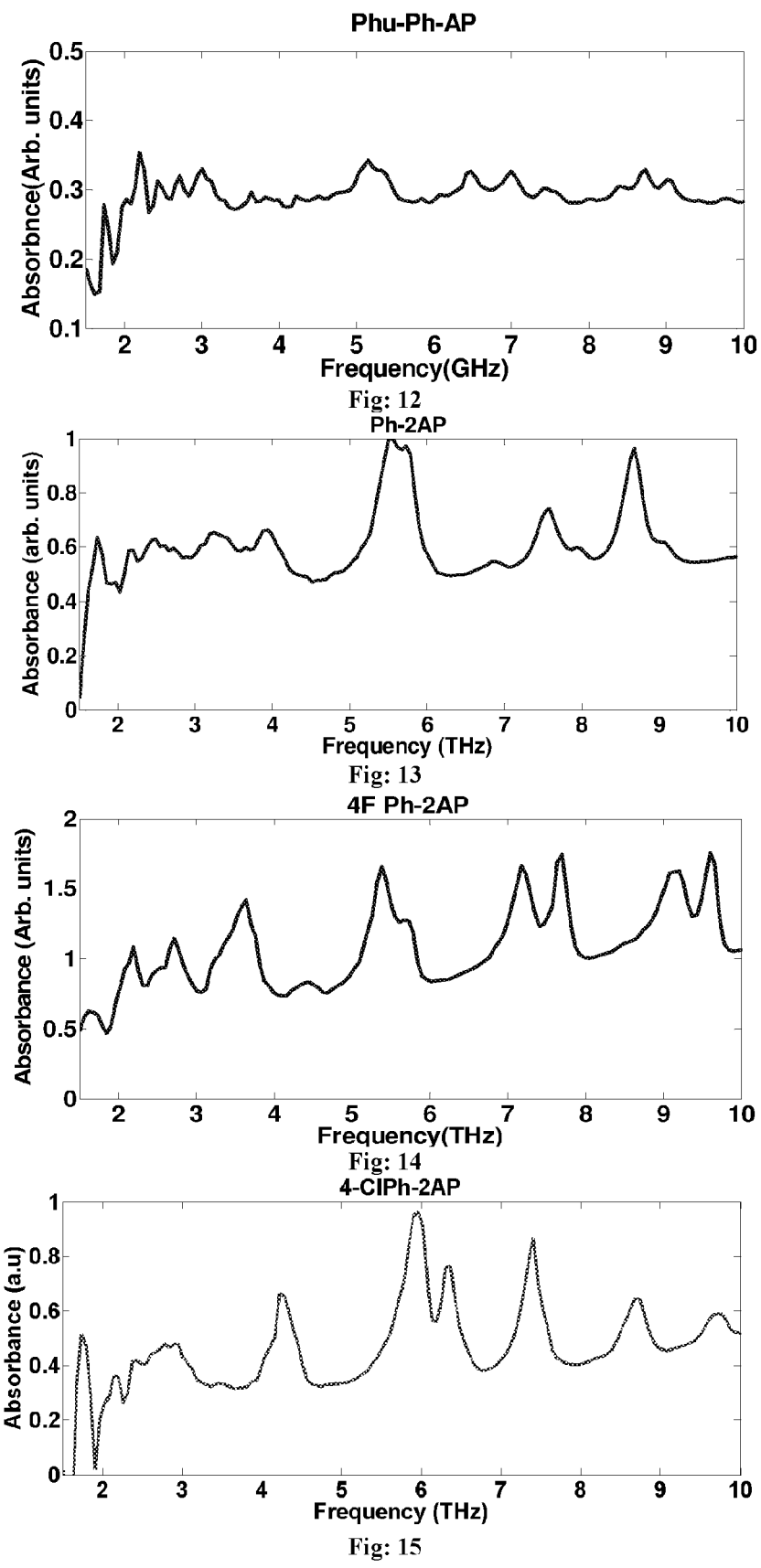
Fig: 12
Fig: 13
Fig: 14
Fig: 15

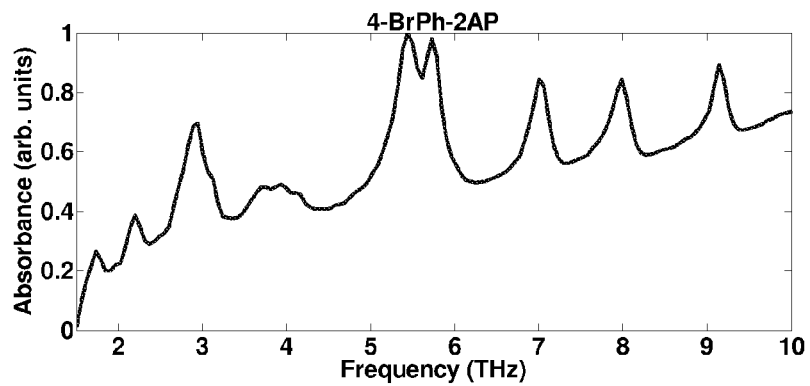
Fig: 16
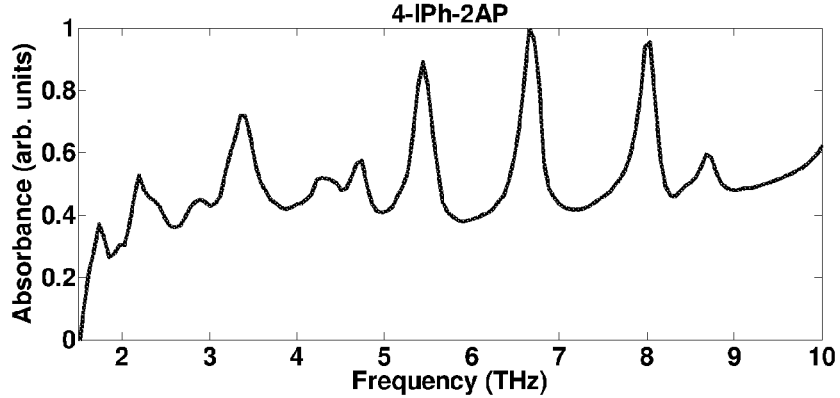
Fig: 17
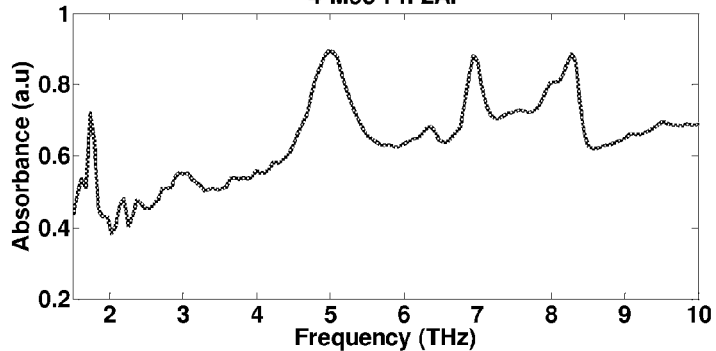
Fig: 18
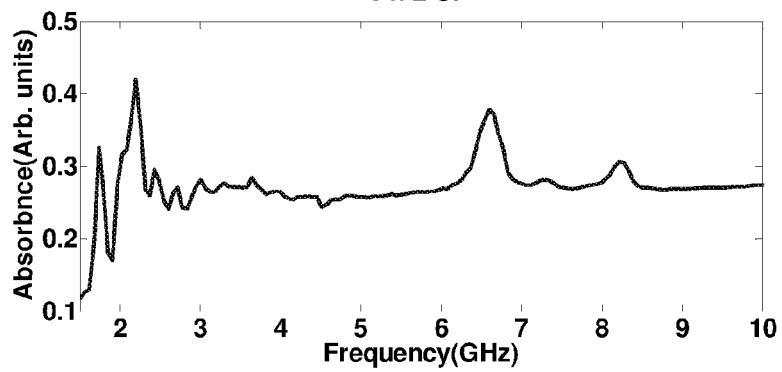
Fig: 19

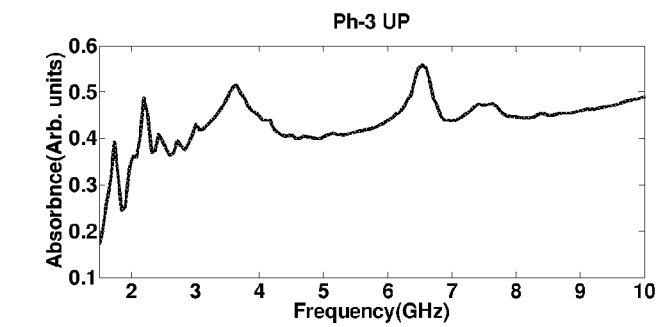
Fig:20
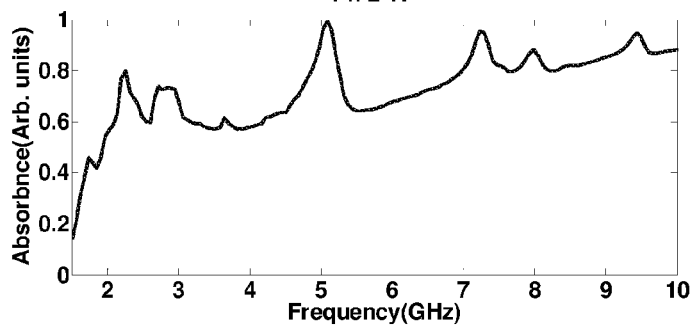
Fig 21
THz spectra of C6-UPh (2-10 THz)
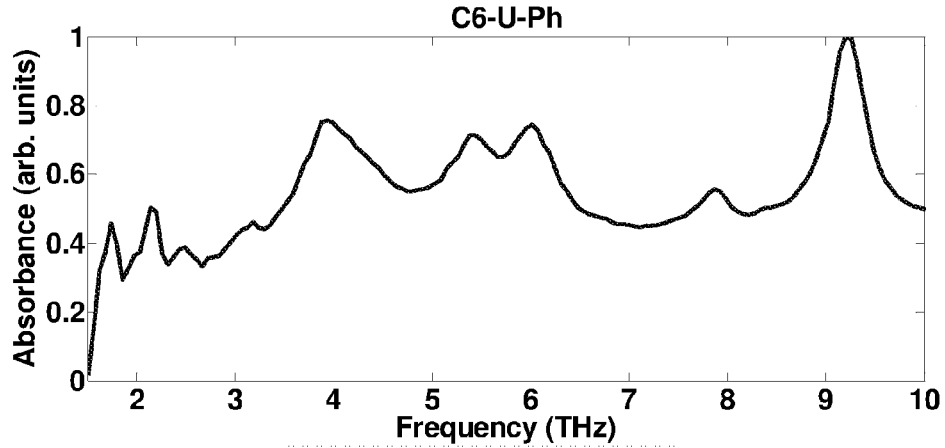
THz spectra of C6-UPh below 1THz
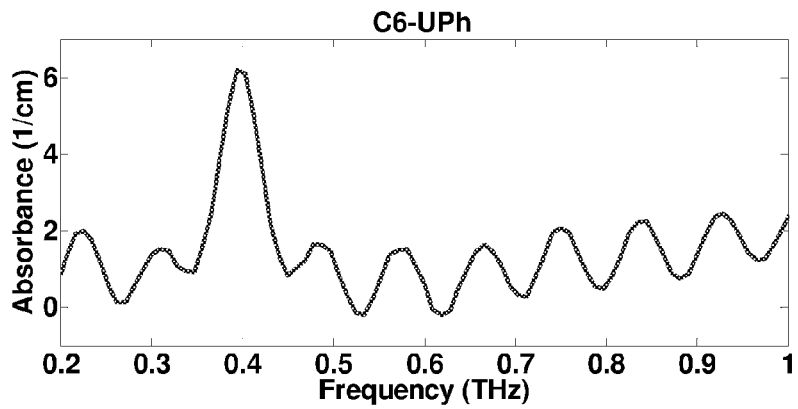
Fig 22

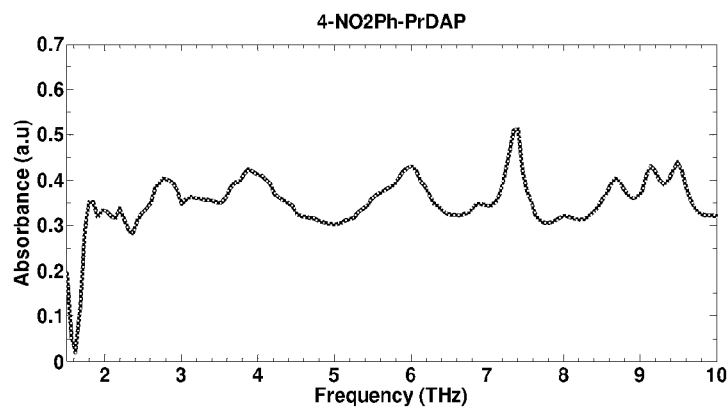
Fig 27
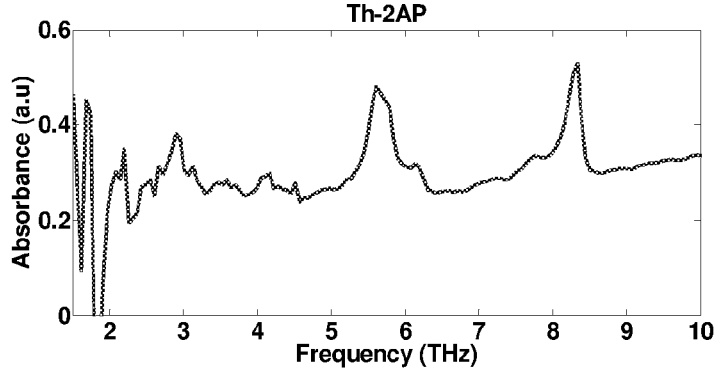
Fig 28
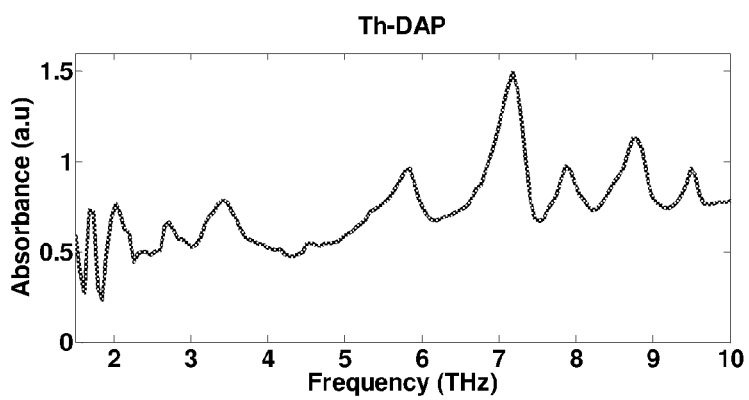
Fig 29
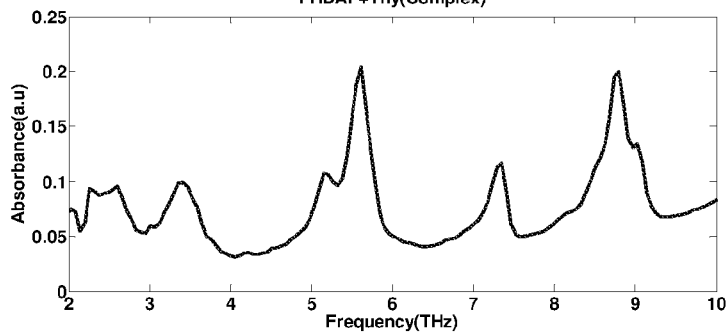
Fig: 30

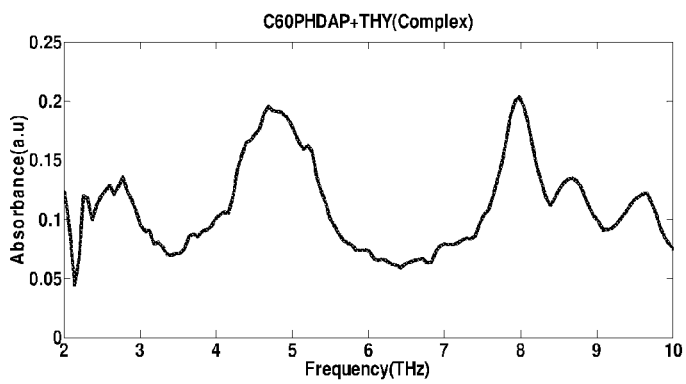
Fig: 31
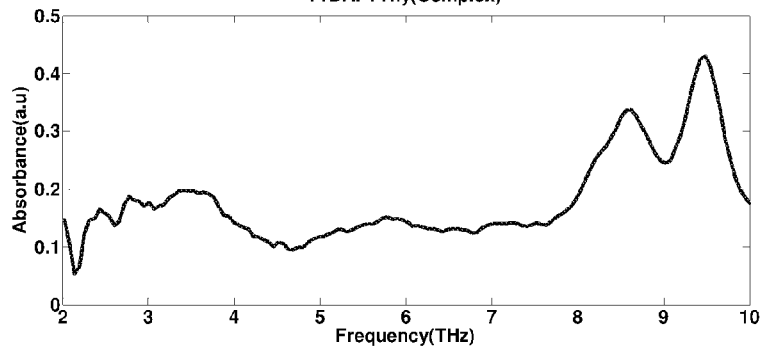
Fig: 32
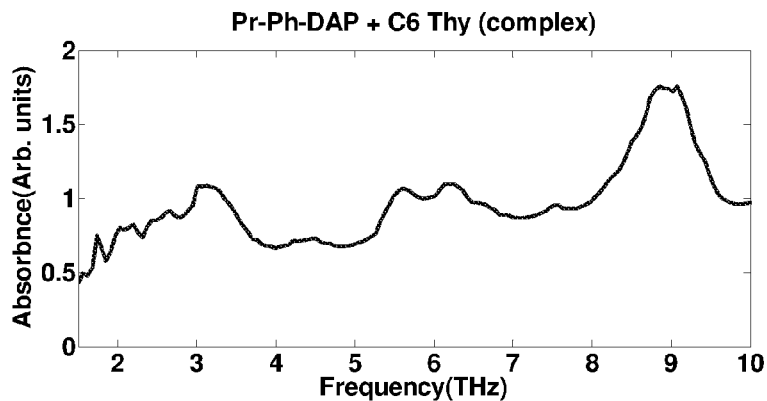
Fig: 33
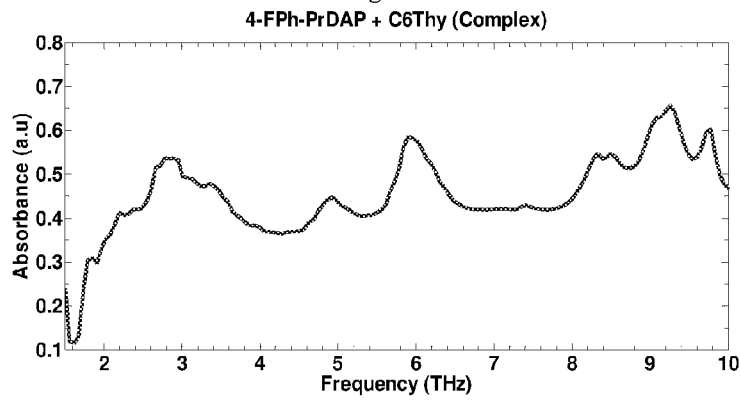
Fig 34

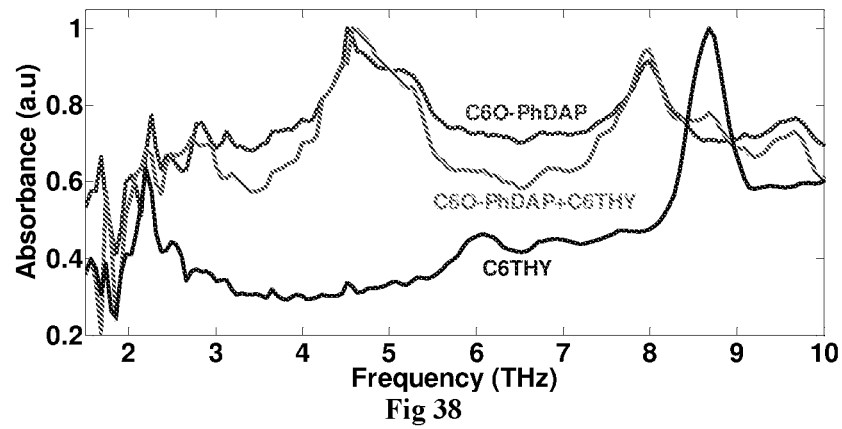
Fig 38
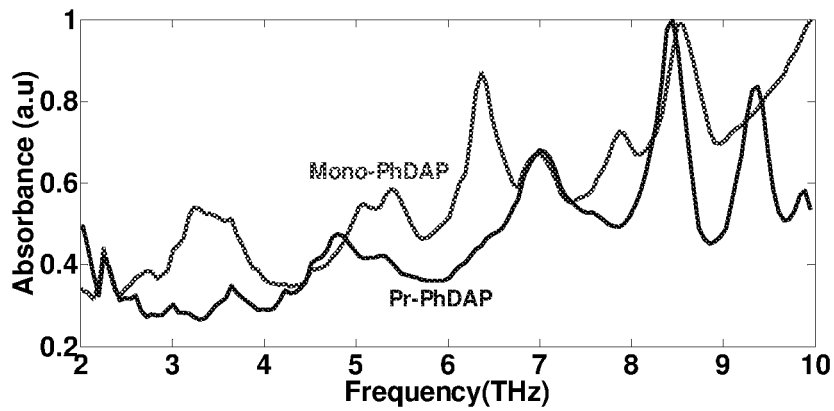
Fig 39
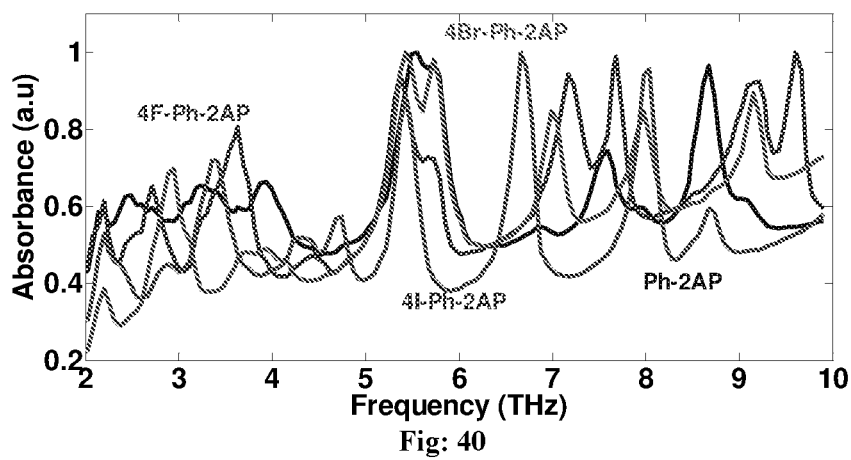
Fig: 40

ORGANIC MOLECULES FOR TERAHERTZ TAGGING APPLICATIONS

FIELD OF THE INVENTION

The present invention relates to heterocyclic and/or aromatic compounds containing amide and/or urea groups and binary molecular complexes based thereon with varying molecular mass and hydrogen bond strengths demonstrating several resonances below 10 THz which are customizable for various applications.

BACKGROUND AND PRIOR ART OF THE INVENTION

THz spectroscopy has been used to study a variety of physical phenomena ranging from atomic transitions to dynamics of biological molecules, and hence involves a wide range of disciplines including physics, chemistry, engineering, astronomy, biology, and medicine.

Terahertz (THz) frequency band lies between the microwave and mid-infrared region of the electromagnetic spectrum. Molecules having strong resonances in this frequency range are ideal for realizing Terahertz tags which can be easily incorporated into various materials. These THz tags find novel use in various counterfeiting applications such as detection of fake currency notes, security documents and counterfeit pharmaceutical drugs, brand protection, and labeling of consumer and industrial products/solutions. The absence of THz signatures for organic materials typically used in consumer/industrial labeling products also makes the present approach advantageous since the embedded THz tags can be easily detected.

THz spectroscopy of molecules, especially at frequencies below 10 THz provides valuable information on the low frequency vibrational modes, viz. intermolecular vibrational modes, intramolecular vibrational modes, hydrogen-bond stretching, torsional vibrations in several chemical and biological compounds. So far there have been very few attempts to engineer molecules which can demonstrate customizable resonances in the THz frequency region.

An article titled, "Application of terahertz spectroscopy and molecular modeling in isomers investigation: Glucose and fructose" by Z.-P. Zheng et al. in Optics Communications 285 (2012) 1868-1871 reports the THz spectra of glucose and fructose in the frequency region from 0.5 to 4.0 THz by THz-TDS at room temperature and employs the gaseous-state theory to simulate the isolated molecules of glucose and fructose.

Another article titled, "Discrimination of Chiral Solids: A Terahertz Spectroscopic Investigation of L- and DL-Serine" by King et al. in J. Phys. Chem. A, 2010, 114, 2945-2953 reports THz absorption spectra from 10 to 90 $cm^{-1}$ for L- and DL-serine along with a complete computational analysis by solid-state DFT using periodic boundary conditions.

Molecules having strong resonances in the THz frequency range are ideal for realizing Terahertz tags. These THz tags find novel use in various anti-counterfeiting applications such as detection of fake currency notes, security documents and counterfeit pharmaceutical drugs, brand protection, and labeling of consumer and industrial products/solutions.

However, there have been very few attempts to engineer molecules which can demonstrate customizable THz resonances. Hence, new molecules with unique and customizable spectroscopic signatures in the Terahertz region are required for incorporation as tags in various anti-counterfeiting applications (currency, pharmaceutical drugs, automotive parts, brand protection, and labeling of consumer and industrial products/solutions, etc.)

OBJECTIVE OF THE INVENTION

The main object of the present invention is to provide organic molecules with various molecular masses and exhibiting various functional groups and tunable strength of various intra/inter-molecular bonds thereby resulting in highly customizable and specific signatures in the Terahertz region (<10 THz).

Another object of the present invention is to provide a simplified methodology to predict novel molecular structures that can result in strong signatures in the THz region.

SUMMARY OF THE INVENTION

Accordingly, present invention provides heterocyclic and/or aromatic compounds containing amide and/or urea groups and binary molecular complexes based on the said compounds with varying mass and intra/inter-molecular, hydrogen bond strengths demonstrating several resonances below 10 THz.

BRIEF DESCRIPTION OF THE DRAWINGS

FIG. 1: THz spectrum of N,N'-(pyridine-2, 6-diyl) dibenzamide (PhDAP) in the range 2-10 THz and below 1 THz.

FIG. 2: THz spectrum of N,N'-(pyridine-2, 6 diyl) dipropionamide (PrDAP).

FIG. 3: THz spectrum of N,N'-(pyridine-2, 6-diyl) bis (4-(hexyloxy) benzamide) (C6OPhDAP).

FIG. 4: THz spectrum of 1-hexyl-5-methylpyrimidine-2, 4(1H, 3H)-dione (C6THY).

FIG. 5: THz spectrum of N-(6-aminopyridin-2-yl) benzamide (mono-PhDAP).

FIG. 6: THz spectrum of N-(6-aminopyridin-2-yl)propionamide (mono-PrDAP).

FIG. 7: THz spectrum of N-(6-propionamidopyridin-2-yl) benzamide (Pr-PhDAP).

FIG. 8: THz spectrum of N-(6-benzamidopyridin-2-yl)-4-nitrobenzamide (4-$NO_2$Ph-PhDAP).

FIG. 9: THz spectrum of 4-nitro-N-(pyridin-2-yl) benzamide (4-$NO_2$Ph-2AP).

FIG. 10: THz spectrum of Di-(pyridin-2-yl) amine (DPA).

FIG. 11: THz spectrum of 1,1'-(ethane-1,2-diyl) bis (3-phenylurea) (PhDUE).

FIG. 12: THz spectrum of N-(6-(3-phenylureido) pyridin-2-yl) benzamide (PhU-PhAP).

FIG. 13: THz spectrum of N-(pyridin-2-yl) benzamide (Ph-2AP).

FIG. 14: THz spectrum of 4-fluoro-N-(pyridin-2-yl) benzamide (4-FPh-2AP).

FIG. 15: THz spectrum of 4-chloro-N-(pyridin-2-yl) benzamide (4-ClPh-2AP).

FIG. 16: THz spectrum of 4-bromo-N-(pyridin-2-yl) benzamide (4-BrPh-2AP).

FIG. 17: THz spectrum of 4-iodo-N-(pyridin-2-yl) benzamide (4-IPh-2AP).

FIG. 18: THz spectrum of 4-methoxy-N-(pyridin-2-yl) benzamide (4-MeOPh-2AP).

FIG. 19: THz spectrum of 1-phenyl-3-(pyridin-2-yl) urea (Ph-2UP).

FIG. 20: THz spectrum of 1-phenyl-3-(pyridin-3-yl) urea (Ph-3UP).

FIG. 21: THz spectrum of 1-phenyl-3-(pyridin-2-yl) thiourea (Ph-2TP).

FIG. 22: THz spectrum of 1-hexyl-3-phenylurea (C6-UPh) in the range 2-10 THz and below 1 THz.

FIG. 27: THz spectrum of 4-nitro-N-(6-propionamidopyridin-2-yl)benzamide (4-NO₂Ph-PrDAP)

FIG. 28: THz spectrum of N-(pyridin-2-yl)thiophene-2-carboxamide (Th-2AP)

FIG. 29: THz spectrum of N,N'-(pyridine-2,6-diyl)bis(thiophene-2-carboxamide) (Th-DAP)

FIG. 30: THz spectrum of PhDAP+C6Thy (1:1 complex).

FIG. 31: THz spectrum of C6OPhDAP+C6Thy (1:1 complex).

FIG. 32: THz spectrum of PrDAP+C6Thy (1:1 complex).

FIG. 33: THz spectrum of Pr-PhDAP+C6Thy (1:1 complex).

FIG. 34: THz spectrum of 4-FPh-PrDAP+C6Thy (1:1 complex).

FIG. 38: THz spectrum of C6OPh-DAP+C6Thy (1:1 complex) overlapped with C6OPhDAP and C6-Thy spectra to demonstrate fine-tuning of resonances.

FIG. 39: THz spectra (overlapped) of monoPhDAP and Pr-PhDAP to demonstrate coarse tuning of Terahertz resonances by functional group substitution.

FIG. 40: THz spectra (overlapped) of Ph-2AP, 4-FPh-2AP, 4-BrPh-2AP and 4-IPh-2AP to demonstrate coarse tuning of Terahertz resonances by functional group substitution.

DETAILED DESCRIPTION OF THE INVENTION

Figure 23:
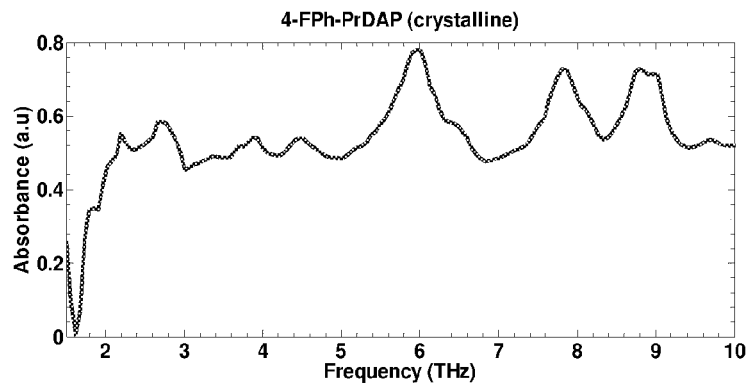
FIG. 23: THz spectrum of 4-fluoro-N-(6-propionamidopyridin-2-yl)benzamide (4-FPh-PrDAP)

Present invention provides several novel substituted heterocyclic and/or aromatic compounds containing amide and/or urea groups and binary molecular complexes based on these compounds. Present invention provides substituted heterocyclic compounds of formula I and/or aromatic compounds of formula II and formula III containing amide and/or urea groups as shown below:

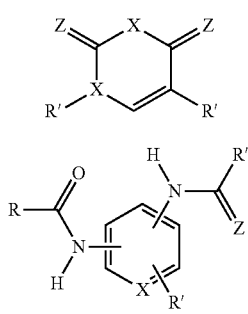

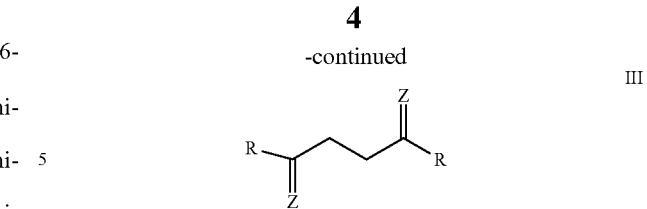

wherein, R is selected from phenyl, Y-Phenyl, pyridyl, thienyl, alkyl;
R' is selected from H, Ar, NHAr, —NHalkyl, Y-Phenyl, thienyl, alkyl, NH₂;
Ar is selected from phenyl, substituted phenyl, pyridyl, substituted pyridyl, substituted thienyl;
X is selected from CH, N, NH;
Y is selected from F, Cl, Br, I, NO₂, alkoxy; and
Z is selected from 0, S.

Present invention provides the substituted heterocyclic and/or aromatic compounds containing amide and/or urea groups exhibiting resonances in the range of 0.1-10 THz. These molecules are herein referred to as THz molecular tags.

The substituted heterocyclic compounds of formula I and/or aromatic compounds of formula II and/or III containing amide and/or urea groups according to invention encompasses the following compounds.

a) N, N'-(pyridine-2, 6-diyl) dibenzamide (PhDAP);
b) N, N'-(pyridine-2, 6 diyl) dipropionamide (PrDAP);
c) N, N'-(pyridine-2, 6-diyl) bis (4-(hexyloxy) benzamide) (C6OPhDAP);
d) 1-hexyl-5-methylpyrimidine-2, 4(1H, 3H)-dione (C6THY);
e) N-(6-aminopyridin-2-yl) benzamide (mono-PhDAP);
f) N-(6-aminopyridin-2-yl)propionamide (mono-PrDAP);
g) N-(6-propionamidopyridin-2-yl) benzamide (Pr-PhDAP);
h) N-(6-benzamidopyridin-2-yl)-4-nitrobenzamide (4-NO2Ph-PhDAP);
i) 4-nitro-N-(pyridin-2-yl) benzamide (4-NO2Ph-2AP);
j) Di-(pyridin-2-yl) amine (DPA);
k) 1,1'-(ethane-1,2-diyl) bis (3-phenylurea) (PhDUE);
l) N-(6-(3-phenylureido) pyridin-2-yl) benzamide (PhU-PhAP);
m) N-(pyridin-2-yl) benzamide (Ph-2AP);
n) 4-fluoro-N-(pyridin-2-yl) benzamide (4-FPh-2AP);
o) 4-chloro-N-(pyridin-2-yl) benzamide (4-ClPh-2AP);
p) 4-bromo-N-(pyridin-2-yl) benzamide (4-BrPh-2AP);
q) 4-iodo-N-(pyridin-2-yl) benzamide (4-IPh-2AP);
r) 4-methoxy-N-(pyridin-2-yl)benzamide (4-MeOPh-2AP);
s) 1-phenyl-3-(pyridin-2-yl) urea (Ph-2UP);
t) 1-phenyl-3-(pyridin-3-yl) urea (Ph-3UP);
u) 1-phenyl-3-(pyridin-2-yl) thiourea (Ph-2TP);
v) 1-hexyl-3-phenylurea (C6-UPh);
w) 4-fluoro-N-(6-propionamidopyridin-2-yl)benzamide (4-FPh-PrDAP);
x) 4-chloro-N-(6-propionamidopyridin-2-yl)benzamide (4-ClPh-PrDAP);
y) 4-bromo-N-(6-propionamidopyridin-2-yl)benzamide (4-BrPh-PrDAP);
z) 4-iodo-N-(6-propionamidopyridin-2-yl)benzamide (4-IPh-PrDAP);
aa) 4-nitro-N-(6-propionamidopyridin-2-yl)benzamide (4-NO₂Ph-PrDAP);
ab) N-(pyridin-2-yl)thiophene-2-carboxamide (Th-2AP); and
ac) N,N'-(pyridine-2,6-diyl)bis(thiophene-2-carboxamide) (Th-DAP).

In another preferred embodiment, the present invention provides a composition comprising substituted heterocyclic and/or aromatic compounds containing amide and/or urea groups exhibiting resonance in the range of 0.1-10 THz which can be used to secure authentication of a product. Accordingly, the invention provides a composition comprising aromatic compounds of formula (I) and/or (II) and/or (III) exhibiting resonances in the range of 0.1-10 THz and the substrate for authentication of a product.

In yet another embodiment, the invention provides a composition comprising aromatic compounds of formula (I) and/or (II) and/or (III) exhibiting resonances in the range of 0.1-10 THz which can be applied on various substrates (metals, plastics etc.) for absorbing Terahertz Radar frequencies.

In yet another aspect, the invention provides a composition comprising aromatic compounds of formula (I) and/or (II) and/or (III) exhibiting resonances in the range of 0.1-10 THz for tailoring refractive index at Terahertz frequencies. Using these compounds, refractive index can also be tuned at Terahertz frequencies.

In yet another embodiment, the present invention provides a pathway for realizing molecules with optimized resonances in THz Radar frequencies, which can be used as absorber/coating materials on various metal/composite/plastic substrates.

In yet another embodiment, the present invention provides a method for customization of resonances in Terahertz frequency region by tuning 1) molecular mass, 2) hydrogen bond strength, 3) inter/intra molecular bonds, 4) isomeric form, and 5) functional group. In yet another embodiment, the invention provides novel substituted heterocyclic compounds of formula I and/or aromatic compounds of formula II or III for authentication of a product, wherein, the authentication of a product comprises detection of fake currency notes, security documents and counterfeit pharmaceutical drugs, brand protection, labeling of consumer and industrial products/solutions etc.

In still another embodiment, the present invention provides a process of authenticating a product by embedding the product with THz tags, substituted heterocyclic and/or aromatic compounds containing amide and/or urea groups, of the present invention, exhibiting resonance in the range of 0.1-10 THz, and detecting the Terahertz tag using a spectrometer/detector.

In an aspect, the present invention provides the solubility of novel substituted heterocyclic and/or aromatic compounds containing amide and/or urea groups in various solvents as shown below in Table: 1 demonstrating the easy incorporation of these THz molecular tags into various substrates:

TABLE 1

| Sr No | Compound | dichloro-methane | Ethyl Acetate | Methanol | DMSO | DMF | THF | Acetone | Toluene | Diethyl Ether |
|---|---|---|---|---|---|---|---|---|---|---|
| 1 | Ph—DAP | S | S | S | S | S | S | S | I | I |
| 2 | Pr—DAP | S | S | S | S | S | S | S | S | S |
| 3 | Mono-Ph—DAP | S | S | S | S | S | S | S | SΔ | I |
| 4 | Mono-Pr—DAP | S | S | S | S | S | S | S | S | S |
| 5 | C6-Thy | S | S | S | S | S | S | S | S | SΔ |
| 6 | Ph—(NO2)—2AP | PS | PS | PS | S | S | S | S | PS | I |
| 7 | 2-2'-DPA | S | S | S | S | S | S | S | S | S |
| 8 | Ph—2UP | S | PS | S | S | S | S | S | PS | PS |
| 9 | PhU—Ph—AP | I | SΔ | I | S | S | S | S | Turbid | Turbid |
| 10 | Ph—3UP | I | SΔ | S | S | S | S | S | I | I |
| 11 | PhU—C2—UPh | I | I | PS | S | S | Turbid | I | I | I |
| 12 | Ph—2TP | S | S | S | S | S | S | S | I | I |
| 13 | 4F—Ph—2AP | S | S | S | S | S | S | S | I | I |
| 14 | 4FPh—PrDAP | S | S | S | S | S | S | S | PS | PS |
| 15 | 4-ClPh—PrDAP | S | S | S | S | S | S | S | PS | PS |
| 16 | 4-BrPh—PrDAP | S | S | S | S | S | S | S | PS | PS |
| 17 | 4-IPh—PrDAP | S | S | S | S | S | S | S | PS | S |
| 18 | 4NO2Ph—PrDAP | S | S | S | S | S | S | S | I | PS |
| 19 | Th—2AP | S | S | S | S | S | S | S | PS | S |
| 20 | Th—DAP | S | S | S | S | S | S | S | I | I |
| 21 | 4Cl—Ph—2AP | S | S | S | S | S | S | S | S | S |
| 22 | 4Br—Ph—2AP | S | S | S | S | S | S | S | S | S |
| 23 | 4I—Ph—2AP | S | S | S | S | S | S | S | S | S |
| 24 | 4-MeO—Ph—2AP | S | S | S | S | S | S | S | S | S |
| 25 | Pr—PhDAP | S | S | S | S | S | S | S | I | PS |
| 26 | 4-NO2—Ph—PhDAP | PS | S | S | S | S | S | S | I | I |
| 27 | C6O—PhDAP | S | S | S | S | S | S | S | S | S |
| 28 | Ph—2AP | S | S | S | S | S | S | S | PS | S |
| 29 | C6—UPh | S | S | S | S | S | S | S | S | S |
| 30 | PhDAP + C6Thy (1:1 complex). | S | S | I | I | I | S | I | I | I |
| 31 | C6OPhDAP + C6Thy (1:1 complex) | S | S | I | I | I | S | I | S | I |
| 32 | PrDAP + C6Thy (1:1 complex) | S | S | I | I | I | S | I | S | I |
| 33 | Pr—PhDAP + C6Thy (1:1 complex) | S | S | I | I | I | S | I | I | I |
| 34 | 4-FPh—PrDAP + C6Thy (1:1 complex) | S | S | I | I | I | S | I | I | I |

TABLE 1-continued

| Sr No | Compound | dichloro-methane | Ethyl Acetate | Methanol | DMSO | DMF | THF | Acetone | Toluene | Diethyl Ether |
|---|---|---|---|---|---|---|---|---|---|---|
| 35 | 4-ClPh—PrDAP + C6Thy (1:1 complex). | S | S | I | I | I | S | I | I | I |
| 36 | 4-BrPh—PrDAP + C6Thy (1:1 complex) | S | S | I | I | I | S | I | I | I |

ABBREVIATIONS
S = Soluble;
I = Insoluble;
PS = Partially Soluble;
SΔ = Soluble on heating at 50° C.
DMSO = dimethyl sulfoxide;
DMF = N,N-dimethyl formamide;
THF = tetrahydrofuran In yet another embodiment, the invention provides binary molecular complexes which comprises the novel substituted heterocyclic compounds of formula I and/or aromatic compounds of formula II and/or III containing amide and/or urea groups together with C6Thy as a second component. Accordingly, the invention encompasses binary molecular complexes selected from the group consisting of PhDAP+C6Thy (1:1 complex); C6OPhDAP+C6Thy (1:1 complex); PrDAP+C6Thy (1:1 complex); and Pr-PhDAP+C6Thy (1:1 complex). All these molecular complexes exhibit resonances in the range of 0.1 to 10 THz whose resonances can be fine-tuned easily.

In yet another embodiment, the invention provides a process of authenticating a product which comprises embedding the product with Binary molecular complexes based on the novel substituted heterocyclic compounds of formula I and/or aromatic compounds of formula II containing amide and/or urea groups according to the invention exhibiting resonance in the range of 0.1-10 THz and detecting the Terahertz tag using a THz spectrometer/THz detector.

For the examples listed below, the prediction of resonances of a molecule in the THz region is carried out using Density Functional Theory (DFT) calculations.

EXAMPLES

Following examples are given by way of illustration and therefore should not be construed to limit the scope of the invention.

Example 1

N, N'-(pyridine-2, 6-diyl) dibenzamide (PhDAP): (FIG. 1)

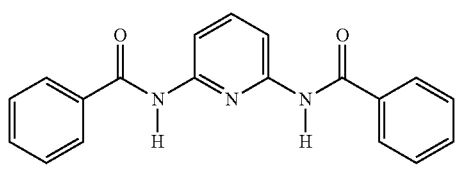 [SMILES: O=C(Nc1cccc(NC(=O)c2ccccc2)n1)c1ccccc1]

Synthetic Procedure:

In a round bottom flask 2, 6-diaminopyridine (1 g, 9.163 mmol) was dissolved in 40 mL of dry dichloromethane and triethylamine (2.8 mL, 27.72 mmol) was added. Then, benzoyl chloride (2.5 mL, 17.98 mmol) was added drop by drop and this mixture was stirred under inert atmosphere at room temperature for 15 h. Reaction mixture was poured in water. Crude product was extracted in dichloromethane, organic layer was washed with water and dried over anhydrous sodium sulphate. The solvent was evaporated on rotary evaporator and crude product was purified by column chromatography on silica gel by eluting with ethyl acetate:hexane (40:60) mixture. The product was further purified by recrystallization using a methanol Yield: 2.60 g (89%).

$^1$H NMR (200 MHz, CDCl$_3$): δ ppm 7.54 (m, 6H), 7.90 (d, 4H, J=6 Hz), 7.82 (t, 1H, J=8 Hz), 8.10 (d, 2H, J=8 Hz), 8.39 (s, 2H).

Example 2

N, N'-(pyridine-2, 6 diyl) dipropionamide (PrDAP): (FIG. 2)

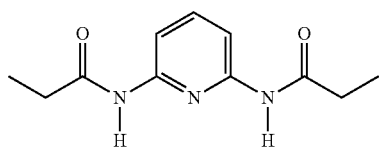 [SMILES: CCC(=O)Nc1cccc(NC(=O)CC)n1]

Synthetic Procedure:

In a round bottom flask 2, 6-diaminopyridine (1 g, 9.163 mmol) was dissolved with 50 mL of dry dichloromethane and triethylamine (2.8 ml, 27.72 mmol) was added, and then propionyl chloride (1.76 ml, 19.02 mmol) was added drop by drop and this mixture was kept in inert atmosphere with stirring at room temp for 15 h. After that reaction mixture was extracted with dichloromethane and washed with water. The organic layer was dried over anhydrous sodium sulphate. Product was purified by column chromatography on Silica gel, by eluting with ethyl acetate:hexane (40:60) mixture. The solvent was evaporated by the rotary evaporator under the reduced pressure and pure product dried in high vacuum. The product was further purified by recrystallization using a mixture of ethyl acetate and hexane (40%). Yield: 1.3 gm, (64.4%).

NMR DATA: $^1$H NMR (200 MHz, CDCl$_3$): δ ppm 1.24 (t, 6H J=8 Hz), 2.39 (q, 4H, J=12 Hz), 1H (s, 7.57), 2H (d, 7.73 J=8 Hz), 2H (d, 7.87, J=8 Hz)

Example 3

N,N'-(pyridine-2,6-diyl)bis(4-(hexyloxy)benzamide) (C6OPhDAP): (FIG. 3)

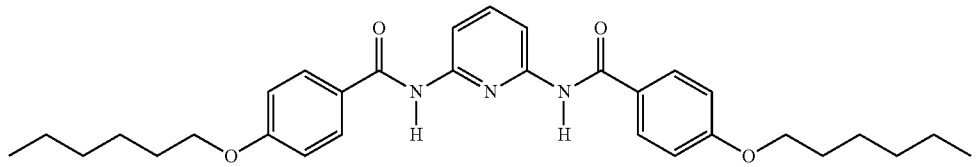 [SMILES: CCCCCCOc1ccc(C(=O)Nc2cccc(NC(=O)c3ccc(OCCCCCC)cc3)n2)cc1]

Step 1
Synthetic Procedure:

In the round bottom flask 4-hydroxy methyl benzoate (2 g, 13.15 mmol) was dissolved in 40 ml of DMF and 1-Bromohexane (2.19 ml, 13.26 mmol) was added. Then potassium carbonate (5.4 g, 39.07 mmol) was added, and refluxed the reaction mixture at 70-80° C. for 15 h. Then the reaction mixture was poured in water and extracted with ethyl acetate. Organic layer was dried over anhydrous sodium sulphate. The product 4-hexyloxy methyl benzoate was purified by column chromatography on silica gel by eluting with 5% ethyl acetate in pet ether and the solvent was evaporated on the rotary evaporator under the reduced pressure and dried in high vacuum. Yield: 2.7 g, (87.1%).

$^1$H NMR (200 MHz, CDCl$_3$): δ ppm, 0.81 (t, 3H), 1.26 (m, 6H), 1.68 (m, 2H, J=6 Hz), 3.87 (m, 5H, J=6 Hz), 6.81 (d, 2H, J=8 Hz), 7.85 (d, 2H, J=8 Hz).

Step 2
Synthetic Procedure:

In the round bottom flask 4-hexyloxy methyl benzoate (2.635 g, 11.158 mmol) dissolved in 25 ml of THF and KOH (3.13 g, 55.93 mmol) dissolved in water (5 ml, 0.278 mmol) was added, and reflux the reaction mixture at 60° C. for 15 h. After the completion of the reaction, neutralised with dil. HCl and the precipitation was filtered and washed with water by extracting with ethyl acetate. The organic layer was dried over anhydrous sodium sulphate. The product 4-hexyloxy benzoic acid was purified by the column chromatography on silica gel by eluting with 20% of ethyl acetate in hexane. The solvent was evaporated on the rotary evaporator under the reduced pressure and dried in high vacuum. Yield: 1.7 g, (68.8%).

$^1$H NMR (200 MHz, CDCl$_3$): δ ppm, 0.91 (t, 3H), 1.37 (m, 6H), 1.81 (t, 2H), 4.02 (t, 3H, J=8 Hz), 6.95 (d, 2H, J=8 Hz), 8.07 (d, 2H, J=8 Hz).

Step 3
Synthetic Procedure:

In round bottom flask 2,6-diaminopyridine (0.340 g, 3.11 mmol) and 4-hexyloxy benzoic acid (1.65 g, 7.42 mmol) was dissolved in 40 mL of dichloromethane. Then 4-dimethylaminopyridine (0.348 g, 2.85 mmol) and EDCI-HCl (0.896 g, 4.67 mmol) were added and stirred under inert atmosphere at room temperature for 24 h. After that reaction mixture was extracted with dichloromethane and the organic layer was washed with water, dried over anhydrous sodium sulphate. The product N,N'-(pyridine-2,6-diyl)bis(4-(hexyloxy)benzamide), was purified by column chromatography on silica gel by eluting with 15% of ethyl acetate in hexane. The solvent was evaporated by rotary evaporator under reduced pressure and dried under high vacuum. Yield: 0.413 g (25.7%).

$^1$H NMR (200 MHz, CDCl$_3$): δppm 0.85 (t, 6H, J=6H), 1.27 (m, 12H, J=6H), 1.75 (q, 4H, J=6H), 3.95 (t, 4H, J=8H), 6.93 (d, 4H, J=10H), 7.81 (m, 7H, J=8H), 8.22 (s, 2H).

Example 4

1-hexyl-5-methylpyrimidine-2,4(1H,3H)-dione (C6THY): (FIG. 4)

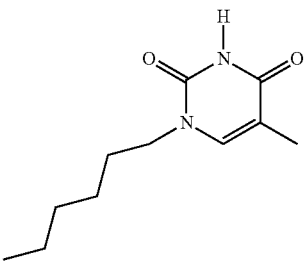

Synthetic Procedure:

In a round bottom flask, thymine (8 g, 63.43 mmol) was dissolved in 60 mL of dimethyl sulfoxide and 1-bromohexane (2.94 mL, 17.81 mmol) and K$_2$CO$_3$ (11.38 g, 82.33 mmol) were added. This mixture was stirred at 70-80° C. for 15 h. The suspension was filtered through sintered funnel, filter cake washed with dichloromethane and filtrate concentrated. The residue obtained was extracted in dichloromethane, washed with water, the organic layer dried over anhydrous sodium sulphate and solvent was evaporated by rotary evaporator under reduced pressure. The crude product was purified by column chromatography on silica with 25% of ethyl acetate in hexane and further purified by recrystallization using a mixture of dichloromethanehexane (30:70). Yield: 6.14 g (38.4%).

NMR DATA: $^1$H NMR (200 MHz, CDCl$_3$): δ ppm 3H (t, 0.88), 6H (m, 1.31), 3H (t, 1.70, J=4 Hz), 3H (s, 1.92, J=6H), 2H (t, 3.68, J=12H), 1H (s, 6.97), 1H (s, 8.70).

Example 5

N-(6-aminopyridin-2-yl)benzamide (mono-PhDAP): (FIG. 5)

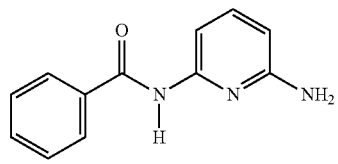 [SMILES: Nc1cccc(NC(=O)c2ccccc2)n1]

Synthetic Procedure:

In a round bottom flask 2,6-diaminopyridine (2.12 g, 19.5 mmol) was dissolved in 40 mL of dry dichloromethane and triethylamine (7.7 mL, 76.23 mmol) was added. Then benzoyl chloride (2.84 mL, 20.43 mmol) was added drop by drop in order to get substitution at one side of 2,6-diaminopyridine and this mixture was kept in inert atmosphere with stirring at room temp for 15 h. Reaction mixture was extracted with dichloromethane and washed with water. The organic layer was dried over anhydrous sodium sulphate and solvent was evaporated on the rotary evaporator. Product purified by column chromatography on silica gel by eluting with ethyl acetate:hexane (30:70). The product was further purified by recrystallization using a mixture of ethyl acetate:hexane (40:60). Yield: 3.75 g (64.1%)

$^1$H NMR (200 MHz, CDCl$_3$): δ ppm 4.34 (s, 2H), 6.31 (d, 1H, J=8 Hz), 7.51 (m, 4H) 7.70 (d, 1H, J=8 Hz), 7.88 (d, 2H, J=6 Hz), 8.28 (s, 1H).

Example 6

N-(6-aminopyridin-2-yl)propionamide (mono-PrDAP): (FIG. 6)

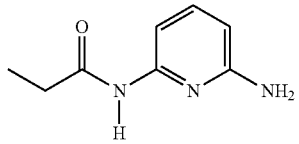

Synthetic Procedure:

In a round bottom flask 2,6-diaminopyridine (5 g, 45.82 mmol) was dissolved in 40 ml of dry dichloromethane and triethylamine (6.43 ml, 63.66 mmol) was added. Then propionoyl chloride (4.00 ml, 43.23 mmol) was added drop by drop in order to get substitution at one side of 2,6-diaminopyridine and this mixture was kept in inert atmosphere with stirring at room temp for 15 h. After that the reaction mixture was extracted with dichloromethane, organic layer was washed with water and dried over anhydrous sodium sulphate. The solvent was evaporated by the rotary evaporator under reduced pressure. Product was purified by column chromatography on silica gel by eluting with 20% ethyl acetate in hexane. The product was further purified by recrystallization using a mixture of 40% ethyl acetate and hexane. Yield: 3.12 g (41%).

Example 7

N-(6-propionamidopyridin-2-yl)benzamide (Pr-PhDAP): (FIG. 7)

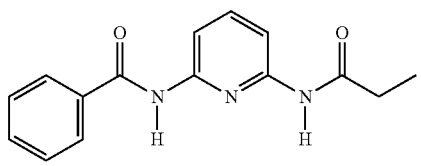 [SMILES: CCC(=O)Nc1cccc(NC(=O)c2ccccc2)n1]

Synthetic Procedure:

In a round bottom flask mono-PrDAP (1 g, 6.06 mmol) was dissolved in 40 mL of dry dichloromethane and triethylamine (1.53 mL, 15.14 mmol) was added. Then benzoyl chloride (1.25 ml, 8.99 mmol) was added dropwise and this mixture was kept in inert atmosphere with stirring at room temperature for 15 h. Then reaction mixture was extracted with dichloromethane and washed with water. The organic layer was dried over anhydrous sodium sulphate and solvent was evaporated on the rotary evaporator under reduced pressure. Product was purified by column chromatography on silica gel by eluting with 40% ethyl acetate in hexane. The product was further purified by recrystallization using a mixture of ethyl acetate and hexane (40:60). Yield: 1.5 g, (68.2%).

$^1$H NMR (200 MHz, CDCl$_3$) δppm 1.25 (t, 3H, J=8 Hz), 2.41 (q, 2H, J=8 Hz), 7.53 (m, 3H), 7.66 (s, 1H), 7.76 (t, 1H, J=8 Hz), 7.88 (m, 2H), 8.05 (d, 1H, J=8 Hz), 8.30 (s, 1H).

Example 8

N-(6-benzamidopyridin-2-yl)-4-nitrobenzamide (4-NO$_2$Ph-PhDAP): (FIG. 8)

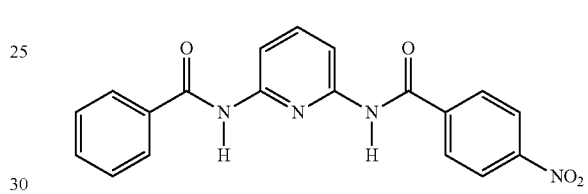

Synthetic Procedure:

In a round bottom flask mono-PhDAP (1 g, 4.69 mmol) and 4-nitrobenzoic acid (1.18 g, 7.06 mmol) were dissolved in 40 mL of N,N-dimethyl formamide and 4-dimethylaminopyridine (0.57 g, 4.66 mmol) and EDCI-HCl (1.82 g, 11.72 mmol) were added under inert atmosphere at room temperature for 24 h. Then reaction mixture was extracted with dichloromethane and washed with water the organic layer was dried over anhydrous sodium sulphate and solvent was evaporated on rotary evaporator under reduced pressure. The product was purified by column chromatography on silica gel by eluting with 50% of ethyl acetate in hexane and dried under high vacuum. Yield: 1.12 g (66%).

$^1$H NMR (200 MHz, CDCl$_3$) δ ppm: 7.57 (m, 3H), 7.84-7.94 (m, 3H), 8.12-8.21 (m, 4H), 8.36 (m, 4H).

Example 9

Synthesis of 4-nitro-N-(pyridin-2-yl)benzamide (4-NO$_2$Ph-2AP): (FIG. 9)

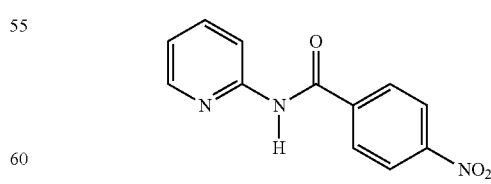

Synthetic Procedure:

In a round bottom flask 2-aminopyridine (1 g, 10.62 mmol) was dissolved in 30 mL of dry N,N-dimethyl formamide and triethylamine (1.6 mL, 15.84 mmol) was added. Then, a solution of 4-nitrobenzoyl chloride (2.96 gm, 15.98 mmol) in dry N,N-dimethyl formamide was added drop by drop and this mixture was kept in inert atmosphere with stirring at room temperature for 24 h. After that the reaction mixture was extracted with dichloromethane and washed with water. The organic layer was dried over anhydrous sodium sulphate and solvent was evaporated by the rotary evaporator under reduced pressure. Product was purified by column chromatography on silica gel by eluting with 30% ethyl acetate in hexane. The product was further purified by recrystallization using a mixture of ethyl acetate and hexane (40:60). Yield: 500 mg (19.4%).

$^1$H NMR (200 MHz, CDCl$_3$): δ ppm 6.81 (t, 1H, J=6 Hz), 7.47 (t, 1H, J=8 Hz), 7.92-8.07 (m, 6H), 10.22 (br s, 1H).

Example 10

Di-(pyridin-2-yl)amine (DPA): (FIG. 10)

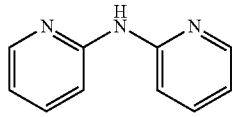 [SMILES: c1ccc(Nc2ccccn2)nc1]

Synthetic Procedure:

The mixture of 2-aminopyridine (4 g, 42.49 mmol) and potassium tert-butoxide (5.72 g, 50.97 mmol) in 60 mL of benzene were refluxed in a 250 mL round bottom flask for 2 h. Then 2-chloropyridine (4.82 mL, 42.45 mmol) was added and continued to reflux for 72 h. Benzene was removed using rotary evaporator. Crude product was extracted with dichloromethane and washed with water. The organic layer was dried over anhydrous sodium sulphate and solvent was evaporated on the rotary evaporator under reduced pressure. Product was purified by column chromatography on silica gel by eluting with 60% ethyl acetate in hexane. Pure product was dried under high vacuum. It was further purified by recrystallization using a mixture of dichloromethane and hexane (25:75). Yield: 2.16 g (30%).

$^1$H NMR (200 MHz, CDCl3): δ ppm: 6.86 (t, 2H, J=6 Hz), 7.59 (m, 4H), 7.81 (s, 1H), 8.26 (d, 2H, J=4 Hz).

Example 11

1,1'-(ethane-1,2-diyl)bis(3-phenylurea) (PhDUE): (FIG. 11)

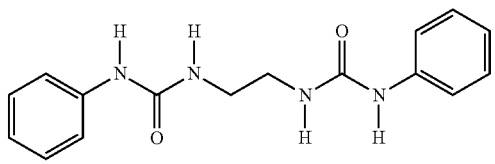 [SMILES: O=C(NCCNC(=O)Nc1ccccc1)Nc1ccccc1]

Synthetic Procedure:

Ethylene diamine (0.55 mL, 9.15 mmol) was taken in 30 mL of dry dichloromethane in two-neck round bottom flask under inert atmosphere. Phenyl isocyanate (2 mL, 16.78 mmol)) was added dropwise. After complete addition, formation of precipitate was observed in reaction mixture. It was stirred at room temperature for 8 h. Completion of reaction was confirmed by thin layer chromatography (TLC). The precipitate was filtered through sintered funnel and washed several times with dichloromethane. The residue was dried under high vacuum. Yield: 2.3 g (94%).

$^1$H NMR (200 MHz, CDCl$_3$): δ ppm: 3.20 (s, 4H), 6.24 (s, 2H), 6.90 (t, 2H, J=6 Hz), 7.39 (m, 8H,), 8.58 (s, 2H).

Example 12

N-(6-(3-phenylureido)pyridin-2-yl)benzamide (PhU-PhAP): (FIG. 12)

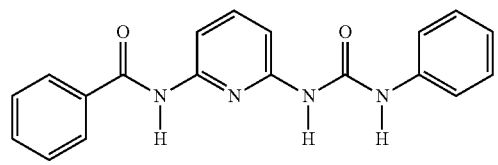 [SMILES: O=C(Nc1ccccc1)Nc1cccc(NC(=O)c2ccccc2)n1]

Synthetic Procedure:

Mono-PhDAP (200 mg, 0.938 mmol) and phenyl isocyanate (0.11 mL, 0.923 mmol) were dissolved in 60 mL of dry dichloromethane. The solution was stirred under reflux in inert atmosphere for 24 h. After this time the solution product precipitated. Reaction mixture was filtered using Whatmann filter paper, residue was washed with dichloromethane and dried under high vacuum. Yield 0.212 g (68%). $^1$H NMR (200 MHz, CDCl$_3$): δ ppm: 7.03 (m, 2H), 7.34 (t, 2H, J=8 Hz), 7.62 (m, 7H), 7.98 (dd, 2H, J=8 Hz), 9.55 (s, 1H), 10.78, 10.84 (d, 2H).

Example 13

Synthesis of N-(pyridin-2-yl)benzamide (Ph-2AP): (FIG. 13)

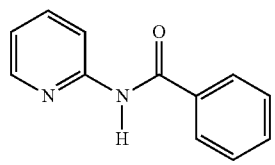 [SMILES: O=C(Nc1ccccn1)c1ccccc1]

Synthetic Procedure:

In a round bottom flask 2-aminopyridine (1 g, 10.62 mmol) was dissolved in 40 mL of dry dichloromethane and triethylamine (1.8 mL, 17.82 mmol) was added. Then, benzoyl chloride (2.21 mL, 15.89 mmol) was added drop by drop and this mixture was stirred under inert atmosphere at room temperature for 15 h. Reaction mixture was poured in water. Crude product was extracted in dichloromethane; organic layer was washed with water and dried over anhydrous sodium sulphate. The solvent was evaporated on rotary evaporator and crude product was purified by column chromatography on silica gel by eluting with ethyl acetate: hexane (20:80) mixture. The product was further purified by recrystallization using methanol Yield: 1.79 g (85.23%).

Example 14

4-fluoro-N-(pyridin-2-yl)benzamide (4-FPh-2AP): (FIG. 14)

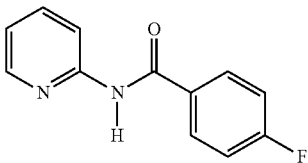 [SMILES: O=C(Nc1ccccn1)c1ccc(F)cc1]

Synthetic Procedure:

In a round bottom flask, 2-aminopyridine (0.5 gm, 5.31 mmol) was dissolved in 40 mL of dry dichloromethane and triethylamine (0.97 mL, 9.60 mmol) was added. Then 4-fluorobenzoyl chloride (0.75 mL, 4.73 mmol) was added drop by drop. During the addition of 4-fluorobenzoyl chloride reaction mixture became pale yellow but turned colourless after complete addition. This mixture was stirred under inert atmosphere at room temperature for 15 h. It was then extracted with dichloromethane, washed with water and organic layer was dried over anhydrous sodium sulphate. The solvent was evaporated by the rotary evaporator under reduced pressure. Crude product was purified by column chromatography on silica gel by eluting with 30% ethyl acetate and hexane and was dried under high vacuum. The product was further purified by recrystallization using a mixture of ethyl acetate:hexane (40:60). Yield: 0.82 g, (72.30%).

$^1$H NMR (200 MHz, CDCl$_3$): δ ppm: 7.08 (t, 3H, J=8 Hz), 7.31 (m, 2H,), 7.82 (m, 3H), 8.43 (d, 2H).

Example 15

4-chloro-N-(pyridin-2-yl)benzamide (4-ClPh-2AP): (FIG. 15)

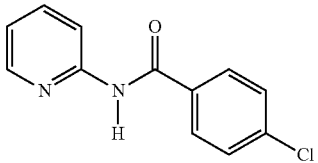 [SMILES: O=C(Nc1ccccn1)c1ccc(Cl)cc1]

In round bottom flask 2-Aminopyridine (0.3 g, 3.19 mmol) and 4-chloro benzoic acid (0.59 g, 3.82 mmol) was dissolved in 20 ml of DMF then HOBt (0.59 g, 3.825 mmol) of added and EDCI-HCl (0.916 g, 4.78 mmol) added in this reaction mixture in inert atmosphere at room temperature for 24 h. After that reaction mixture washed with water by extracting with DCM, the organic layer was dried over anhydrous sodium sulphate. The product 4-chloro-N-(pyridin-2-yl) benzamide was purified by the column chromatography on silica gel by eluting with 25% of ethyl acetate and hexane. The solvent was evaporated by rotary evaporator under reduced pressure and dried under high vacuum. Yield=0.46 g (63.30%).

$^1$H NMR (200 MHz, CDCl$_3$): δ ppm 7.12 (t, 1H, J=8 Hz), 7.50 (d, 2H, J=8 Hz), 7.77 (t, 1H, J=8 Hz), 7.86 (d, 2H, J=8 Hz), 8.28 (d, 1H, J=4 Hz), 8.39 (d, 1H, J=8 Hz), 8.76 (br, s, 1H).

Example 16

4-bromo-N-(pyridin-2-yl)benzamide (4-BrPh-2AP): (FIG. 16)

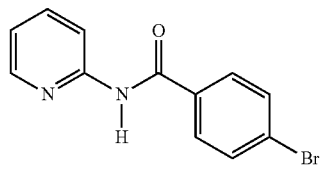 [SMILES: O=C(Nc1ccccn1)c1ccc(Br)cc1]

Synthetic Procedure:

In round bottom flask 2-aminopyridine (1 g, 10.62 mmol) and 4-bromobenzoic acid (2.56 g, 12.73 mmol) was dissolved in 40 mL of dichloromethane. Then Hydrocybenzotiazol (HOBt) (1.95 g, 12.73 mmol) and EDCI-HCl (3.05 g, 15.91 mmol) were added and stirred under inert atmosphere at room temperature for 24 h. After that reaction mixture was extracted with dichloromethane and the organic layer was washed with water, dried over anhydrous sodium sulphate. The product was purified by column chromatography on silica gel by eluting with 15% of ethyl acetate in hexane. The solvent was evaporated by rotary evaporator under reduced pressure and dried under high vacuum. Yield: 1.4 g (45.2%).

$^1$H NMR (200 MHz, CDCl$_3$): δ ppm: 7.08 (t, 1H, J=8 Hz), 7.64 (d, 2H, J=8 Hz), 7.80 (m, 3H), 8.25 (d, 1H, J=4 Hz), 8.36 (d, 1H, J=8 Hz), 8.85 (br s, 1H).

Example 17

4-iodo-N-(pyridin-2-yl)benzamide (4-IPh-2AP): (FIG. 17)

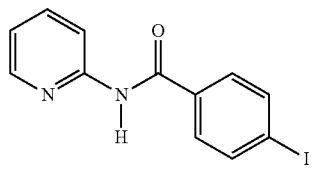 [SMILES: O=C(Nc1ccccn1)c1ccc(I)cc1]

Synthetic Procedure:

In round bottom flask 2-aminopyridine (0.3 g, 3.18 mmol) and 4-Iodobenzoic acid (0.95 g, 3.83 mmol) was dissolved in 40 mL of dichloromethane. Then Hydrocybenzotiazol (HOBt) (0.59 g, 3.85 mmol) and EDCI-HCl (0.91 g, 4.74 mmol) were added and stirred under inert atmosphere at room temperature for 24 h. After that reaction mixture was extracted with dichloromethane and the organic layer was washed with water, dried over anhydrous sodium sulphate. The product was purified by column chromatography on silica gel by eluting with 15% of ethyl acetate in hexane. The solvent was evaporated by rotary evaporator under reduced pressure and dried under high vacuum. Yield: 0.5 g g (50%).

$^1$H NMR (200 MHz, CDCl$_3$): δ ppm: 7.12 (t, 1H, J=8 Hz), 7.66-7.88 (m, 5H), 8.27 (d, 1H, J=4 Hz), 8.44 (d, 1H, J=10 Hz), 9.04 (br s, 1H).

Example 18

4-methoxy-N-(pyridin-2-yl)benzamide (4-MeOPh-2AP): (FIG. 18)

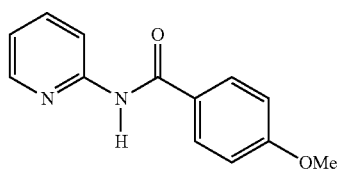 [SMILES: COc1ccc(C(=O)Nc2ccccn2)cc1]

In round bottom flask 2-Aminopyridine (0.3 g, 3.18 mmol) and 4-methoxybenzoic acid (0.58 gm, 3.82 mmol) was dissolved in 30 ml of DMF then HOBt (0.59 g, 3.82 mmol) and EDCI-HCl (0.91 g, 4.78 mmol) was added in this reaction mixture in inert atmosphere at room temperature for 24 h. After that reaction mixture washed with water by extracting with DCM, the organic layer was dried over anhydrous sodium sulphate. The product 4-methoxy-N-(pyridin-2-yl)benzamide, was purified by the column chromatography on silica gel by eluting with 30% of ethyl acetate and hexane. The solvent was evaporated by rotary evaporator under reduced pressure and dried under high vacuum. Yield=0.5 gm (69%).

$^1$H NMR (400 MHz, CDCl$_3$): δ ppm 3.95 (s, 3H), 7.09 (d, 2H, J=8 Hz), 7.49 (m, 3H), 8.08 (d, 1H, J=8 Hz), 8.26 (d, 2H, J=8 Hz).

Example 19

1-phenyl-3-(pyridin-2-yl)urea (Ph-2UP): (FIG. 19)

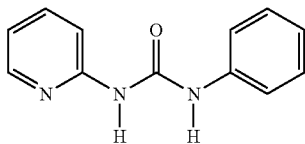 [SMILES: O=C(Nc1ccccc1)Nc1ccccn1]

Synthetic Procedure:

2-aminopyridine (200 mg, 2.12 mmol) and phenyl isocyanate (0.26 mL, 2.18 mmol) were dissolved in 50 mL of dry dichloromethane. The solution was stirred under reflux for 24 h. Reaction mixture was concentrated under reduced pressure, resulting in the precipitation of a white solid that was isolated by filtration and washed by dichloromethane. Further concentration of the filtrate gave a second batch of the product. Yield: 0.29 g (64%).

$^1$H NMR (200 MHz, CDCl$_3$): δ ppm 6.96 (t, 2H, J=8 Hz), 7.11 (t, 1H, J=6 Hz), 7.37 (t, 2H, J=8 Hz), 7.62 (d, 3H, J=8 Hz), 8.26 (d, 1H, J=4 Hz), 9.14 (s, 1H), 11.83 (s, 1H).

Example 20

1-phenyl-3-(pyridin-3-yl)urea (Ph-3UP): (FIG. 20)

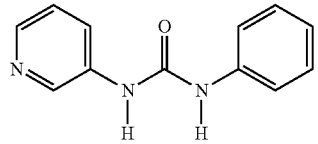 [SMILES: O=C(Nc1ccccc1)Nc1cccnc1]

Synthetic Procedure:

3-aminopyridine (200 mg, 2.12 mmol) and phenyl isocyanate (0.26 mL, 2.18 mmol) were dissolved in 60 mL of dry dichloromethane. The solution was refluxed under inert atmosphere for 24 h while stirring. The precipitate obtained during reaction was filtered through Whatmann filter paper, washed with dichloromethane and dried under high vacuum. Yield 0.313 g (69%).

$^1$H NMR (200 MHz, CDCl$_3$): δ ppm 7.01 (t, 1H, J=8 Hz), 7.31 (m, 3H), 7.47 (d, 2H, J=8 Hz), 7.96 (dd, 1H, J=6 Hz), 8.20 (dd, 1H, J=4 Hz), 8.63 (d, 1H), 8.87 (d, 2H, J=8 Hz).

Example 21

1-phenyl-3-(pyridin-2-yl)thiourea (Ph-2TP): (FIG. 21)

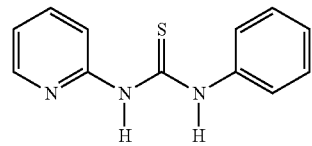 [SMILES: S=C(Nc1ccccc1)Nc1ccccn1]

Synthetic Procedure:

2-Aminopyridine (200 mg, 2.12 mmol) and phenyl isothiocyanate (0.28 mL, 2.07 mmol) were dissolved in 50 mL of dry dichloromethane. The solution was refluxed under inert atmosphere for 36 h while stirring. Reaction mixture was concentrated under reduced pressure, the residue was recrystallized by using mixture of dichloromethane and hexane (20:80). Yield: 0.208 g (42%).

$^1$H NMR (200 MHz, CDCl$_3$): δ ppm 6.89 (s, 1H), 7.01 (t, 1H, J=2 Hz), 7.25 (m, 2H), 7.41 (t, 2H, J=4 Hz), 7.66 (d, 3H), 8.21 (d, 1H), 8.98 (s, 1H).

Example 22

1-hexyl-3-phenylurea (C6-UPh): (FIG. 22)

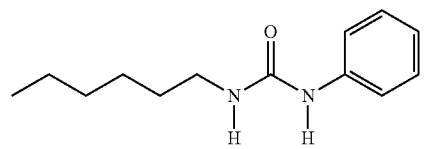 [SMILES: CCCCCCNC(=O)Nc1ccccc1]

Synthetic Procedure:

n-Hexyl amine (0.26 mL, 1.97 mmol) and phenyl isocyanate (0.26 mL, 2.18 mmol) were dissolved in 50 mL of dry dichloromethane. The solution was stirred under reflux for 24 h. After this time the solution was concentrated under reduced pressure, the residue was recrystallized by using a mixture of dichloromethane and hexane (20:80). Yield: 0.208 g (42%).

$^1$H NMR (200 MHz, CDCl$_3$) δppm 0.78 (t, 3H), 1.16-1.36 (m, 8H), 3.07 (t, 2H), 4.47 (br, s, 1H) 6.94 (q, 1H), 7.18 (m, 4H).

Example 23

4-fluoro-N-(6-propionamidopyridin-2-yl)benzamide (4-FPh-PrDAP): (FIG. 23)

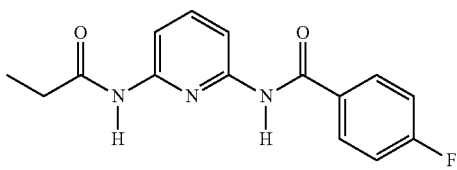 [SMILES: CCC(=O)Nc1cccc(NC(=O)c2ccc(F)cc2)n1]

In the round bottom flask mono Pr-DAP (0.3 g, 1.81 mmol) was dissolved in 40 ml of dry DCM and triethylamine (0.31 mL, 2.18 mmol) was added. Then 4-fluorobenzoyl chloride (0.26 mL, 2.18 mmol) was added drop by drop. This mixture was kept in inert atmosphere with stirring at room temp for 15 h. After that, reaction mixture was washed with water by extracting with DCM. The organic layer was dried over anhydrous sodium sulphate. Product purified by column chromatography on silica gel by eluting with 30% ethyl acetate and hexane. The solvent was evaporated by the rotary evaporator under reduced pressure and pure product was dried under high vacuum. Yield: 0.49 g (94%).

$^1$H NMR (400 MHz, CDCl$_3$): δ ppm 1.26 (t, 3H, J=8 Hz), 2.43 (q, 2H, J=8 Hz), 7.19 (t, 2H, J=8 Hz), 7.72 (br, s, 1H), 7.78 (t, 1H, J=8 Hz), 7.93 (m, 3H), 8.03 (t, 1H, J=8 Hz), 8.27 (br, s, 1H).

Example 24

Figure 24:
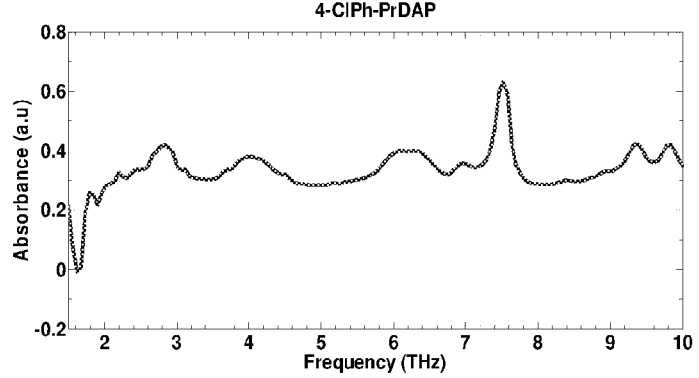
FIG. 24: THz spectrum of 4-chloro-N-(6-propionamidopyridin-2-yl)benzamide (4-ClPh-PrDAP)

4-chloro-N-(6-propionamidopyridin-2-yl)benzamide (4-ClPh-PrDAP): (FIG. 24)

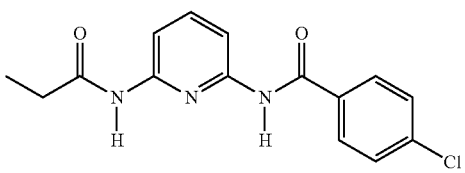 [SMILES: CCC(=O)Nc1cccc(NC(=O)c2ccc(Cl)cc2)n1]

In the round bottom flask mono Pr-DAP (0.2 g, 1.21 mmol) was dissolved in 40 ml of dry dichloromethane and triethylamine (0.20 mL, 1.45 mmol) was added. Then 4-chlorobenzoyl chloride (0.187 mL, 1.45 mmol) was added drop by drop. This mixture was kept in inert atmosphere with stirring at room temp for 15 h. Then it was extracted with DCM and washed with water. The organic layer was dried over anhydrous sodium sulphate. Product was purified by column chromatography on silica gel by eluting with 30% ethyl acetate in hexane. The solvent was evaporated under reduced pressure and dried under high vacuum. Yield: 0.21 g (56%).

$^1$H NMR (400 MHz, CDCl$_3$): δ ppm 1.27 (t, 3H, J=8 Hz), 2.44 (q, 2H, J=8 Hz), 7.50 (d, 2H, J=8 Hz), 7.72 (s, 1H), 7.78 (t, 1H, J=8 Hz), 7.84 (d, 2H, J=8 Hz), 7.97 (d, 1H, J=8 Hz), 8.04 (d, 1H, J=8 Hz), 8.26 (s, 1H).

Example 25

Figure 25:
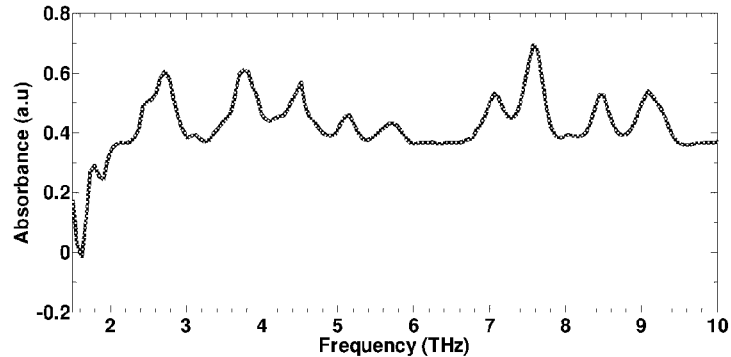
FIG. 25: THz spectrum of 4-bromo-N-(6-propionamidopyridin-2-yl)benzamide (4-BrPh-PrDAP)

4-bromo-N-(6-propionamidopyridin-2-yl)benzamide (4-BrPh-PrDAP): (FIG. 25)

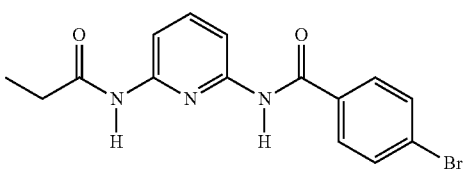 [SMILES: CCC(=O)Nc1cccc(NC(=O)c2ccc(Br)cc2)n1]

In the round bottom flask mono Pr-DAP (0.2 g, 1.21 mmol) was dissolved in 40 ml of dry dichloromethane and triethylamine (0.20 mL, 1.45 mmol) was added. Then 4-bromobenzoyl chloride (0.32 gm, 1.45 mmol) in dry DCM was added drop by drop. This mixture was kept in inert atmosphere with stirring at room temp for 15 h. After that, reaction mixture was washed with water by extracting with DCM. The organic layer was dried over anhydrous sodium sulphate. Product purified by column chromatography on silica gel by eluting with 30% ethyl acetate and hexane. The solvent was evaporated by the rotary evaporator under reduced pressure and pure product was dried under high vacuum. Yield: 0.24 g (57%).

$^1$H NMR (200 MHz, CDCl$_3$): δ ppm 1.27 (t, 3H, J=8 Hz), 2.42 (q, 2H, J=8 Hz), 7.59 (d, 2H, J=8 Hz), 7.67 (m, 2H), 7.75, 7.79 (m, 3H), 7.95 (d, 2H, J=8 Hz), 8.02 (d, 1H, J=8 Hz), 8.20 (s, 1H).

Example 26

Figure 26:
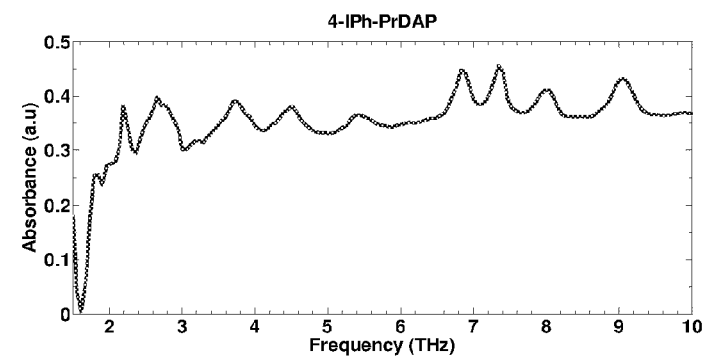
FIG. 26: THz spectrum of 4-iodo-N-(6-propionamidopyridin-2-yl)benzamide (4-IPh-PrDAP)
Figure 35:
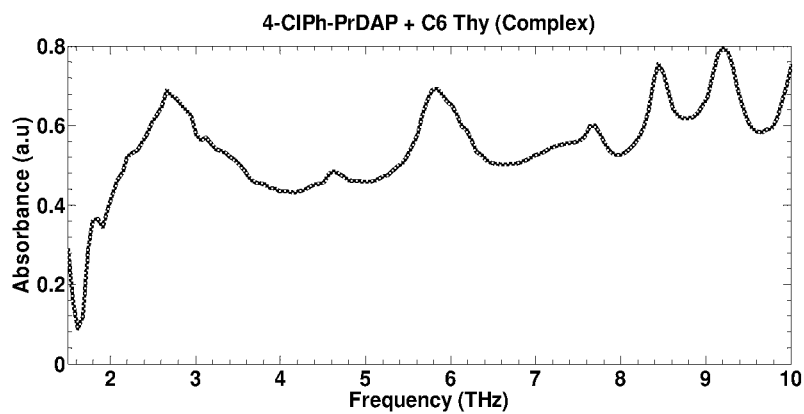
FIG. 35: THz spectrum of 4-ClPh-PrDAP+C6Thy (1:1 complex).
Figure 36:
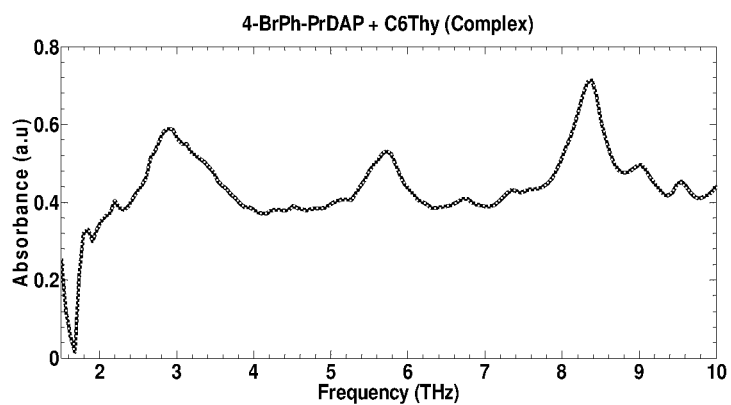
FIG. 36: THz spectrum of 4-BrPh-PrDAP+C6Thy (1:1 complex).

4-iodo-N-(6-propionamidopyridin-2-yl)benzamide (4-IPh-PrDAP): (FIG. 26)

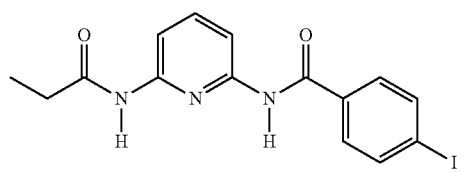 [SMILES: CCC(=O)Nc1cccc(NC(=O)c2ccc(I)cc2)n1]

In the round bottom flask mono Pr-DAP (0.2 g, 1.21 mmol) was dissolved in 40 ml of dry dichloromethane and triethylamine (0.25 mL, 1.81 mmol) was added. Then 4-iodobenzoyl chloride (0.48 gm, 1.81 mmol) in dry DCM was added drop by drop. This mixture was kept in inert atmosphere with stirring at room temp for 15 h. After that, reaction mixture was washed with water after extracting with DCM. The organic layer was dried over anhydrous sodium sulphate. Product purified by column chromatography on silica gel by eluting with 30% ethyl acetate and hexane. The solvent was evaporated by the rotary evaporator under reduced pressure and pure product was dried under high vacuum. Yield: 0.26 g (55%).

$^1$H NMR (200 MHz, CDCl$_3$): δ ppm 1.27 (t, 3H, J=8 Hz), 2.43 (q, 2H, J=8 Hz), 7.59 (d, 2H, J=8 Hz), 7.60 (d, 2H, J=8

Hz), 7.77, (t, 1H, J=8 Hz), 7.85 (d, 2H, J=8 Hz), 7.95 (d, 1H, J=10 Hz), 8.02 (d, 1H, J=10 Hz), 8.20 (s, 1H).

Example 27

4-nitro-N-(6-propionamidopyridin-2-yl)benzamide (4-NO$_2$Ph-PrDAP): (FIG. 27)

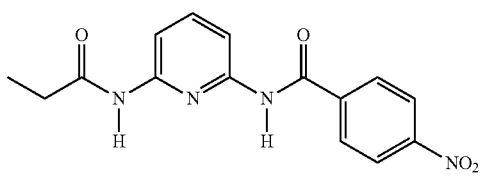 [SMILES: CCC(=O)Nc1cccc(NC(=O)c2ccc([N+](=O)[O-])cc2)n1]

Mono Pr-DAP (0.1 g, 0.6 mmol) was added in ethyl acetate 25 mL, purified by washing with 5% sodium carbonate solution, saturated sodium chloride solution, drying over anhydrous magnesium sulphate. Mixture of mono-Pr-DAP and purified ethyl acetate was cooled to 5° C. Then triethyl amine (0.1 mL, 0.72 mmol) was added. Then 4-nitrobenzoyl chloride (0.14 g, 0.72 mmol) dissolved in purified ethyl acetate was added drop wise at such a rate to maintain the temperature below 10° C. The ice bath was removed upon complete addition of 4-nitro benzoyl chloride solution and the reaction stirred for 24 hours. The reaction mixture was then filtered on a by Whitman filter paper. The filtrate washed three times with 5% NaOH solution and once with water, to remove unreacted 4-Nitrobenzoyl chloride, and washed once with saturated sodium chloride, dried over anhydrous magnesium sulphate, filtered through sodium sulphate funnel. The solvent was evaporated by the rotary evaporator under reduced pressure and pure product was dried under high vacuum. Yield: 0.11 g (58%).

$^1$H NMR (400 MHz, CDCl$_3$): δ ppm 1.27 (t, 3H, J=8 Hz), 2.43 (q, 2H, J=8 Hz), 7.60 (brs, 1H), 7.80 (t, 1H, J=8 Hz), 8.10 (m, 4H), 8.35 (m, 3H).

Example 28

N-(pyridin-2-yl)thiophene-2-carboxamide (Th-2AP): (FIG. 28)

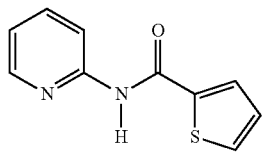 [SMILES: O=C(Nc1ccccn1)c1cccs1]

In the round bottom flask thiophene-2-carboxylic acid (1 g, 7.8 mmol) was dissolved in 30 mL of dry dichloromethane and thionyl chloride (0.74 mL, 10.1 mmol) was added slowly by dropping funnel followed by 1-2 drops of dry DMF. This mixture was kept in inert atmosphere with stirring at room temp for 24 h. After that, all the solvent was removed by vacuum distillation without heating the reaction mixture. In two necked round bottom flask 2AP (0.2 g, 2.12 mmol) was dissolved in dry dichloromethane, and dry pyridine (0.22 mL, 2.76 mmol) was added. This reaction mixture was stirred for 15 min. Previously made thiophene-2-carbonyl chloride (0.4 g, 2.76 mmol) was added drop by drop to the amine containing reaction mixture and stirred for 24 h. Completion of reaction was confirmed by TLC, reaction mixture was washed with water and extracted in dichloromethane. The organic layer was dried over anhydrous sodium sulphate. Product was purified by column chromatography on silica gel by eluting with 30% ethyl acetate in hexane. The solvent was evaporated under reduced pressure and dried under high vacuum. Yield: =0.37 g (75%).

$^1$H NMR (400 MHz, CDCl$_3$): δ ppm 7.08 (t, 1H, J=HZ), 7.16 (t, 1H, J=HZ), 7.59 (d, 1H, J=8 Hz), 7.72 (d, 1H, J=Hz), 7.77 (t, 1H, J=8 Hz), 8.33 (d, 2H, J=8 Hz), 8.61 (br s, 1H).

Example 29

N,N'-(pyridine-2,6-diyl)bis(thiophene-2-carboxamide) (Th-DAP): (FIG. 29)

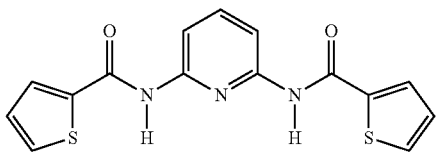 [SMILES: O=C(Nc1cccc(NC(=O)c2cccs2)n1)c1cccs1]

In the round bottom flask thiophene-2-carboxylic acid (1 g, 7.8 mmol) was dissolved in 30 mL of dry dichloromethane and thionyl chloride (0.74 mL, 10.1 mmol) was added slowly by dropping funnel followed by 1-2 drops of dry DMF. This mixture was kept in inert atmosphere with stirring at room temp for 24 h. After that, all the solvent was removed by vacuum distillation without heating the reaction mixture. In two necked round bottom flask 2,6-DAP (0.2 g, 1.83 mmol) was dissolved in dry dichloromethane, and dry pyridine (0.32 mL, 4.03 mmol) was added. This reaction mixture was stirred for 15 min. Previously made thiophene-2-carbonyl chloride (0.43 g, 4.03 mmol) was added drop by drop to the amine containing reaction mixture and stirred for 24 h. Completion of reaction was confirmed by TLC, reaction mixture was washed with water and extracted in dichloromethane. The organic layer was dried over anhydrous sodium sulfate. Product was purified by column chromatography on silica gel by eluting with 30% ethyl acetate in hexane. The solvent was evaporated under reduced pressure and dried under high vacuum. Yield: =0.51 g (85%).

$^1$H NMR (400 MHz, CDCl$_3$): δ ppm 7.14 (t, 2H, J=4 Hz), 7.58, 7.65 (dd, 4H), 7.77 (t, 1H, J=8 Hz), 8.01 (d, 2H, J=8 Hz), 8.19 (s, 2H).

Example 30

Hydrogen Bonded Complexes of Heterocomplementary Pairs (DAP and C6THY)
General Procedure for Preparation of Complexes:
Equimolar mixture of N,N'-diacylamino pyridine (DAP derivative) and C6THY was prepared in minimum amount of chloroform by mixing solutions of the two compounds prepared in chloroform separately. The solution mixture was stirred at room temperature for 10 min to allow for complex formation. Solvent was evaporated on rotary evaporator under vacuum at room temperature and dried under high vacuum. The solid obtained was used for spectroscopic studies.

1. PhDAP + C6Thy (1:1 complex) : (FIG: 30)
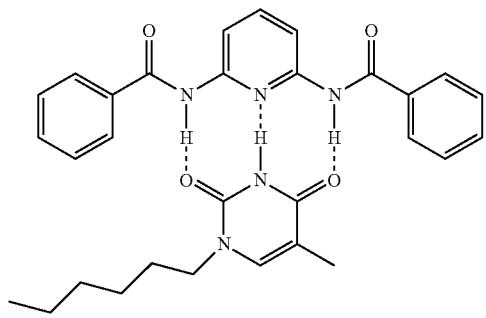
2. C6OPhDAP + C6Thy (1:1 complex) : (FIG: 31)
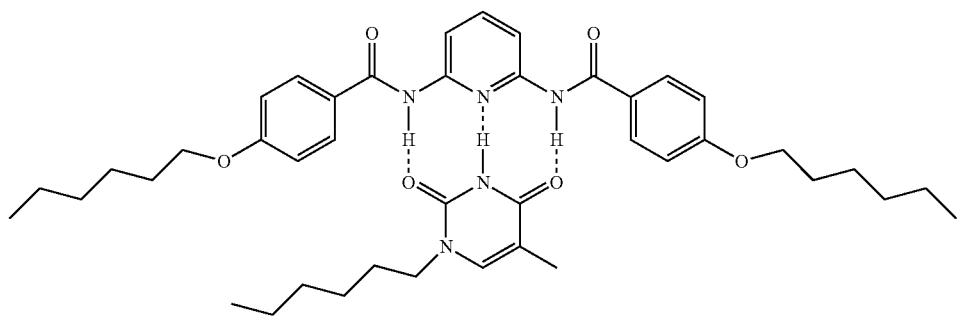
3. PrDAP + C6Thy (1:1 complex) : (FIG: 32)
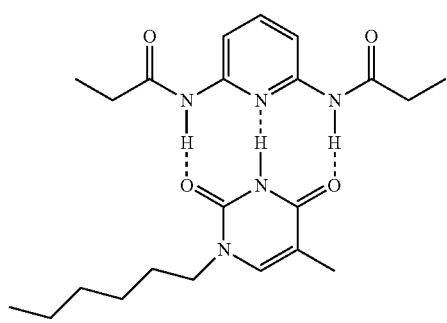
4. Pr-PhDAP + C6Thy (1:1 complex) : (FIG: 33)
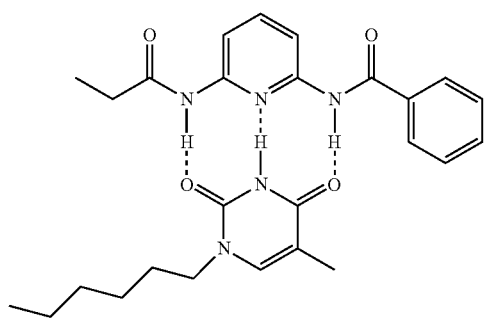

Example 31

Figure 37:
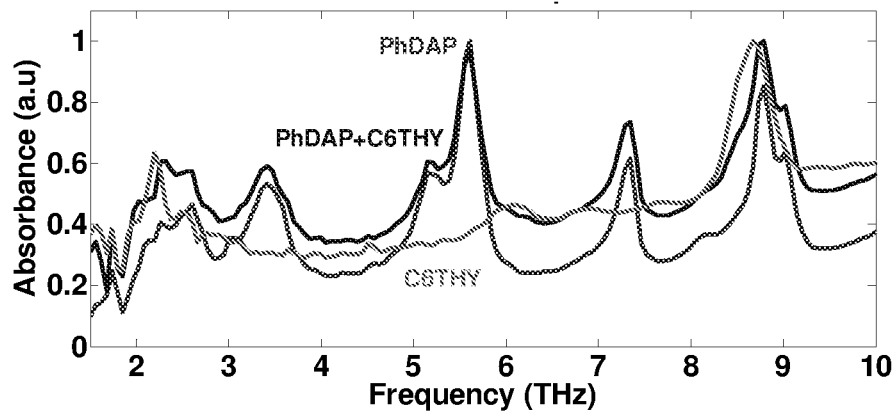
FIG. 37: THz spectrum of Ph-DAP+C6Thy (1:1 complex) overlapped with PhDAP and C6-Thy spectra to demonstrate fine-tuning of resonances.

Fine Tuning of THz Resonances by Using Hydrogen Bonded Complexes
1. THz spectrum of Ph-DAP+C6Thy (1:1 complex) overlapped with PhDAP and C6-Thy spectra. FIG. 37)
2. THz spectrum of C6OPh-DAP+C6Thy (1:1 complex) overlapped with C6OPhDAP and C6-Thy spectra. (FIG. 38)

Example 32

Coarse Tuning of Terahertz Resonances by Functional Group Substitution
1. THz spectra (overlapped) of monoPhDAP and Pr-PhDAP to demonstrate coarse tuning of Terahertz resonances by functional group substitution (FIG. 39).
2. THz spectra (overlapped) of Ph-2AP, 4-FPh-2AP, 4-BrPh-2AP and 4-IPh-2AP to demonstrate coarse tuning of Terahertz resonances by functional group substitution (FIG. 40).

ADVANTAGES OF THE INVENTION a. Tagging of products is easier by using the novel substituted heterocyclic and/or aromatic compounds containing amide and/or urea groups.
b. Customizable resonances in the range of 0.1 to 10 THz.

We claim:

1. A method of detecting a Terahertz resonance signature in a product comprising:
  embedding a compound in the product, wherein the compound functions as a Terahertz tag, and
  using Terahertz spectroscopy to detect resonance of the tagged product in the range of 0.1-10 THz,
  wherein the compound is selected from the group consisting of:
  a. N, N'-(pyridine-2, 6 diyl) dipropionamide (PrDAP);
  b. N, N'-(pyridine-2, 6-diyl) bis (4-(hexyloxy) benzamide) (C6OPhDAP);
  c. N-(6-aminopyridin-2-yl)propionamide (mono-PrDAP);
  d. N-(6-propionamidopyridin-2-yl) benzamide (Pr-Ph-DAP);
  e. N-(6-benzamidopyridin-2-yl)-4-nitrobenzamide (4-NO2Ph-PhDAP);
  f. N-(6-(3-phenylureido) pyridin-2-yl) benzamide (PhU-PhAP);
  g. 4-fluoro-N-(pyridin-2-yl) benzamide (4-FPh-2AP);
  h. 4-iodo-N-(pyridin-2-yl) benzamide (4-IPh-2AP);
  i. 1-phenyl-3-(pyridin-2-yl) urea (Ph-2UP);
  j. 1-phenyl-3-(pyridin-3-yl) urea (Ph-3UP);
  k. 1-phenyl-3-(pyridin-2-yl) thiourea (Ph-2TP);
  l. 1-hexyl-3-phenylurea (C6-UPh);
  m. 4-fluoro-N-(6-propionamidopyridin-2-yl)benzamide (4-FPh-PrDAP);
  n. 4-chloro-N-(6-propionamidopyridin-2-yl)benzamide (4-ClPh-PrDAP);
  o. 4-bromo-N-(6-propionamidopyridin-2-yl)benzamide (4-BrPh-PrDAP);
  p. 4-iodo-N-(6-propionamidopyridin-2-yl)benzamide (4-IPh-PrDAP);
  aa. 4-nitro-N-(6-propionamidopyridin-2-yl)benzamide (4-NO2Ph-PrDAP);
  bb. N-(pyridin-2-yl)thiophene-2-carboxamide (Th-2AP); and
  cc. N,N'-(pyridine-2,6-diyl)bis(thiophene-2-carboxamide) (Th-DAP).

2. A method of detecting a Terahertz resonance signature in a product comprising:
  embedding a binary molecular complex in the product, wherein the binary molecular complex comprises a primary component and a secondary component, wherein the binary molecular complex functions as a Terahertz tag, and
  using Terahertz spectroscopy to detect resonance of the tagged product in the range of 0.1-10 THz,
  wherein the primary component is selected from the group consisting of:
  a. N, N'-(pyridine-2, 6 diyl) dipropionamide (PrDAP);
  b. N, N'-(pyridine-2, 6-diyl) bis (4-(hexyloxy) benzamide) (C6OPhDAP);
  c. N-(6-aminopyridin-2-yl)propionamide (mono-PrDAP);
  d. N-(6-propionamidopyridin-2-yl) benzamide (Pr-Ph-DAP);
  e. N-(6-benzamidopyridin-2-yl)-4-nitrobenzamide (4-NO2Ph-PhDAP);
  f. N-(6-(3-phenylureido) pyridin-2-yl) benzamide (PhU-PhAP);
  g. 4-fluoro-N-(pyridin-2-yl) benzamide (4-FPh-2AP);
  h. 4-iodo-N-(pyridin-2-yl) benzamide (4-IPh-2AP);
  i. 1-phenyl-3-(pyridin-2-yl) urea (Ph-2UP);
  j. 1-phenyl-3-(pyridin-3-yl) urea (Ph-3UP);
  k. 1-phenyl-3-(pyridin-2-yl) thiourea (Ph-2TP);
  l. 1-hexyl-3-phenylurea (C6-UPh);
  m. 4-fluoro-N-(6-propionamidopyridin-2-yl)benzamide (4-FPh-PrDAP);
  n. 4-chloro-N-(6-propionamidopyridin-2-yl)benzamide (4-ClPh-PrDAP);
  o. 4-bromo-N-(6-propionamidopyridin-2-yl)benzamide (4-BrPh-PrDAP);
  p. 4-iodo-N-(6-propionamidopyridin-2-yl)benzamide (4-IPh-PrDAP);
  aa. 4-nitro-N-(6-propionamidopyridin-2-yl)benzamide (4-NO2Ph-PrDAP);
  bb. N-(pyridin-2-yl)thiophene-2-carboxamide (Th-2AP); and
  cc. N,N'-(pyridine-2,6-diyl)bis(thiophene-2-carboxamide) (Th-DAP), and
  wherein the secondary component of the bimolecular complex is selected from the group consisting of C6Thy and Di-(pyridin-2-yl) amine (DPA).

3. The method according to claim 2, wherein the binary molecular complex is selected from the group consisting of:
  a) N,N'-(pyridine-2,6-diyly) dibenzamide (PhDAP)+ C6Thy (1:1 complex);
  b) N, N'-(pyridine-2, 6-diyl) bis (4-(hexyloxy) benzamide) (C6OPhDAP)+(C6Thy) (1:1 complex);
  c) N, N'-(pyridine-2, 6 diyl) dipropionamide (PrDAP)+ (C6Thy) (1:1 complex);
  d) N-(6-propionamidopyridin-2-yl) benzamide (Pr-Ph-DAP)+(C6Thy) (1:1 complex);
  e) 4-fluoro-N-(6-propionamidopyridin-2-yl)benzamide (4-FPh-PrDAP)+(C6Thy) (1:1 complex);
  f) 4-chloro-N-(6-propionamidopyridin-2-yl)benzamide (4-ClPh-PrDAP)+(C6Thy) (1:1 complex); and
  g) 4-bromo-N-(6-propionamidopyridin-2-yl)benzamide (4-BrPh-PrDAP)+(C6Thy) (1:1 complex).

4. The method according to claim 1, wherein the product is a currency note, a security document, a pharmaceutical, a consumer product, a label on a consumer product, an industrial product or a label on an industrial product.

5. The method according to claim 2, wherein the product is a currency note, a security document, a pharmaceutical, a consumer product, a label on a consumer product, an industrial product or a label on an industrial product.

* * * * *